US009662404B2

(12) United States Patent
Pellois

(10) Patent No.: US 9,662,404 B2
(45) Date of Patent: May 30, 2017

(54) COMPOSITIONS AND METHODS FOR THE DELIVERY OF MOLECULES INTO LIVE CELLS

(71) Applicant: The Texas A&M University System, College Station, TX (US)

(72) Inventor: Jean-Philippe Pellois, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 14/482,946

(22) Filed: Sep. 10, 2014

(65) Prior Publication Data

US 2015/0099690 A1   Apr. 9, 2015

Related U.S. Application Data

(60) Provisional application No. 61/876,006, filed on Sep. 10, 2013.

(51) Int. Cl.
*A61K 47/48* (2006.01)

(52) U.S. Cl.
CPC .............................. *A61K 47/48315* (2013.01)

(58) Field of Classification Search
None
See application file for complete search history.

(56) References Cited

U.S. PATENT DOCUMENTS

| 2009/0186802 A1 | 7/2009 | Alluis |
| 2011/0300111 A1 | 12/2011 | White |
| 2012/0142584 A1 | 6/2012 | Bonny |

FOREIGN PATENT DOCUMENTS

| WO | 99/47173 A2 | 9/1999 |
| WO | 2012047354 A2 | 4/2012 |
| WO | 2012090150 A2 | 7/2012 |

OTHER PUBLICATIONS

Erazo-Oliveras et al. Nature Methods. vol. 11, No. 8; p. 861-867. Jun. 15, 2014.*
Erazo-Oliveras et al. Nature Methods. vol. 11, No. 8; Supplementary Figures. Jun. 15, 2014.*
Pan et al. Mol Biol Rep. 37(4): 2117-2124. Apr. 2010.*
Matsumoto et al. Bioorganic & Medicinal Chemistry Letters 10 (2000) 1857-1861.*
Angeles-Boza, A.M., et al., "Generation of Endosomolytic Reagents by Branching of Cell-Penetrating Peptides: Tools for the Delivery of Bioactive Compounds to Live Cells in Cis or Trans," Bioconjugte Chemistry 21(12):2164-2167, Dec. 2011. (Author Manuscript providedf, PMCID: PM3074029, available in PMC Dec. 15, 2011, 8 pages).
Austin, C.D., et al., "Oxidizing Potential of Endosomes and Lysosomes Limits Intracellular Cleavage of Disulfide-Based Antibody-Drug Conjugates," Proceedings of the National Academy of Sciences of the USA (PNAS) 102(50):17987-17992, Dec. 2005.
Csaszar, E., et al., "An Automated System for Delivery of an Unstable Transcrition to Hematopoietic Stem Cell Cultures," Biotechnology and Bioengineering 103(2):402-412, Jun. 2009.
Dietz, G.P.H., and M. Bähr, "Delivery of Bioactive Molecules Into the Cell: The Trojan Horse Approach," Molecular and Cellular Neuroscience 27(2):85-131, Oct. 2004.
Domashenko, A.D. et al., "TAT-Mediated Transduction of NF-Ya Peptide Induces the Ex Vivo Proliferation and Engraftment Potential of Human Hematopoietic Progenitor Cells," Blood 116(15):2676-2683, Oct. 2010.
Dominska, M., and D.M. Dykxhoorn, "Breaking Down the Barriers: siRNA Delivery and Endosome Escape," Journal of Cell Science 123(Pt 8):1183-1189, Apr. 2010.
Eguchi, A., et al., "Efficient siRNA Delivery Into Primary Cells by Peptide Transduction-dsRNA Binding Domain (PTD-DRBD) Fusion Protein," Nature: Biotechnology 27(6):567-571, Jun. 2009. (Author Manuscript provided, PMCID: PMC2694965, available in PMC Dec. 1, 2009, 12 pages).
Erazo-Oliveras, A., et al., "Improving the Endosomal Escape of Cell-Penetrating Peptides and Their Cargos: Strategies and Challenges," Pharmaceuticals 5(11):1177-1209, Nov. 2012.
Fischer, R., et al., "Break on Through to the Other Side—Biophysics and Cell Biology Shed Light on Cell-Penetrating Peptides," ChemBioChem 6(12):2126-2142, Dec. 2006.
Green, I., et al., "Protein Transduction Domains: Are They Delivering?" Trends in Pharmacological Sciences 24(5):213-215, May 2003.
Gump, J.M., et al., "Revised Role of Glycosaminoglycans in TAT Protein Transduction Domain-Mediated Cellular Transduction," Journal of Biological Chemistry 285(2):1500-1507, Jan. 2010.
Hoyer, J., "Dimerization of a Cell-Penetrating Peptide Leads to Enhanced Cellular Uptake and Drug Delivery," Beilstein Journal of Organic Chemistry 8:1788-1797, Oct. 2012.
Krosl, J., et al., "In Vitro Expansion of Hematopoietic Stem Cells by Recombinant TAT-HOXB4 Protein," Nature: Medicine 9(11):1428-1432, Nov. 2003.
Lee, Y.-J., et al., "Delivery of Macromolecules Into Live Cells by Simple Co-Incubation With a Peptide," ChemBioChem 11(3):325-330, Feb. 2010. (Author Manuscript provided, PMCID: PMC2916931, available in PMC Feb. 11, 2011, 14 pages.)
Lee, Y.-J., et al., "A HA2-Fusion Tag Limits the Endosomal Release of Its Protein Cargo Despite Causing Endosomal Lysis," Biochim Biophys Acta 1810(8):752-758, Aug. 2011. (Author Manuscript provided, PMCID: PMC3128663, available in PMC Aug. 1, 2012, 15 pages.)
Michiue, H., et al., "The $NH_2$ Terminus of Influenza Virus Hemagglutinin-2 Subunit Peptides Enhances the Antitumor Potency of Polyarginine-Mediated p53 Protein Transduction," Journal of Biological Chemistry 280(9):8285-8289, Mar. 2005.
Muthukrishnan, N., et al., "Synergy Between Cell-Penetrating Peptides and Singlet Oxygen Generators Leads to Efficient Photolysis of Membranes," Photochemical Photobiology 89(3):625-630, May 2013. (Author Manuscript provided, PMCID: PMC3622158, available in PMC May 1, 2014, 12 pages.)

(Continued)

*Primary Examiner* — Amber D Steele
*Assistant Examiner* — Schuyler Milton
(74) *Attorney, Agent, or Firm* — Christensen O'Connor Johnson Kindness PLLC

(57) ABSTRACT

The present disclosure provides methods and compositions related to the cytosolic delivery of proteins and cell-impermeable small molecules into live cells using an endosomolytic dimer of cell-penetrating peptide TAT.

31 Claims, 27 Drawing Sheets

(56) References Cited

OTHER PUBLICATIONS

Muthukrishnan, N., et al., "TAT-Mediated Photochemical Internalization Results in Cell Killing by Causing the Release of Calcium Into the Cytosol of Cells," Biochimica et Biophysica Acta 1820(11):1734-1743, Nov. 2012.

Peitz, M., et al., "Ability of the Hydrophobic FGF and Basic TAT Peptides to Promote Cellular Uptake of Recombinant Cre Recombinase: A Tool for Efficient Genetic Engineering of Mammalian Genomes," Proceedings of the National Academy of Sciences of the USA (PNAS) 99(7):4489-4494, Apr. 2002.

Poon, G.M.K., and J. Gariépy, "Cell-Surface Proteoglycans as Molecular Portals for Cationic Peptide and Polymer Entry Into Cells," Biochemical Society Transactions 35(Pt 4):788-793, Aug. 2007.

Schwarze, S.R., et al., "Protein Transduction: Unrestricted Delivery Into All Cells?" trends in Cell Biology 10(7):290-295, Jul. 2000.

Srinivasan, D., et al., "Conjugation to the Cell-Penetrating Peptide TAT Potentiates the Photodynamic Effect of Carboxytetramethylrhodamine," PLoS One 6(3):e17732, Mar. 2011, pp. 1-10.

Sung, M., et al., "The Importance of Valency in Enhancing the Import and Cell Routing Potential of Protein Transduction Domain-Containing Molecules," Biochimica et Biophysica Acta 1758(3):355-363, Mar. 2006.

Tung, C.-H., et al., "Novel Branching Membrane Translocational Peptide as Gene Delivery Vector," Bioorganic & Medicinal Chemistry 10(11):3609-3614, Nov. 2002.

Wadia, J.S., et al., "Transducible TAT-HA Fusogenic Peptide Enhances Escape of TAT-Fusion Proteins After Lipid Raft Macropinocytosis," Nature Medicine 10(3):310-315, Mar. 2004.

Zhang, H., et al., "Reprogramming of Somatic Cells via TAT-Mediated Protein Transduction of Recombinant Factors," Biomaterials 33(20):5047-5055, Jul. 2012.

International Search Report dated Dec. 31, 2014, issued in corresponding International Application No. PCT/US2014/055021, filed Sep. 10, 2014, 4 pages.

Chugh, A., et al., "Translocation of Cell-Penetrating Peptides and Delivery of Their Cargoes in Triticale Microspores," Plant Cell Reports 28(5):801-810, May 2009.

Jones, A.T., and E.J. Sayers, "Cell Entry of Cell Penetrating Peptides: Tales of Tails Wagging Dogs," Journal of Controlled Release 161(2):582-591, Jul. 2012.

Lee, S.-J., et al., "Enhancement of Gene Delivery Using Novel Homodimeric Tat Peptide Formed by Disulfide Bond," Journal of Microbiology and Biotechnology 21(8):802-807, Aug. 2011.

Partial Supplementary European Search Report, mailed Mar. 27, 2017, in corresponding EP Application No. 14843936.7, filed Sep. 10, 2014, 8 pages.

Rudolph, C., et al., "Application of Novel Solid Lipid Nanoparticle (SLN)-Gene Vector Formulations Based on a Dimeric HIV-1 TAT-Peptide in Vitro and in Vivo," Pharmaceutical Research 21(9):1662-1669, Sep. 2004.

Wan, L., et al., "Novel Multi-Component Nanopharmaceuticals Derived From Poly(ethylene) Glycol, Retro-Inverso-Tat Nonapeptide and Saquinavir Demonstrate Combined Anti-HIV Effects," AIDS Research and Therapy 3:12, Dec. 2006, 15 pages.

\* cited by examiner

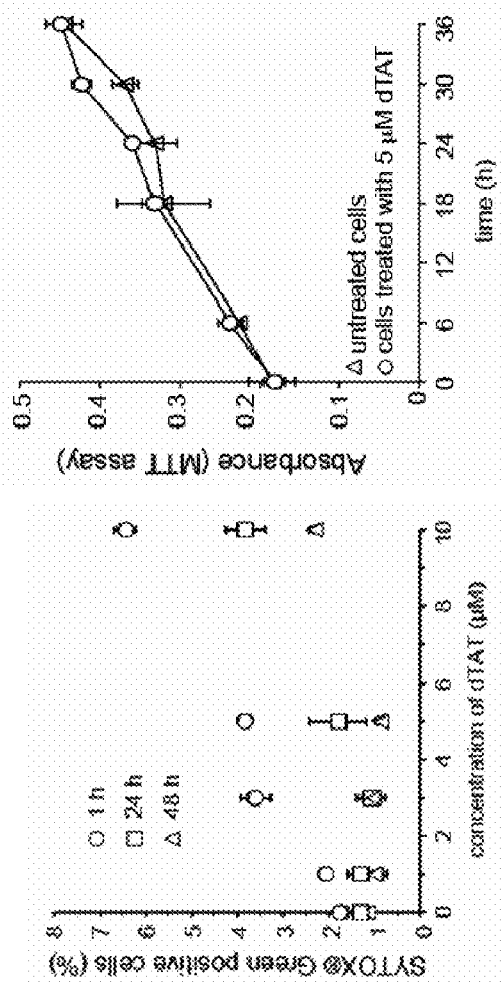
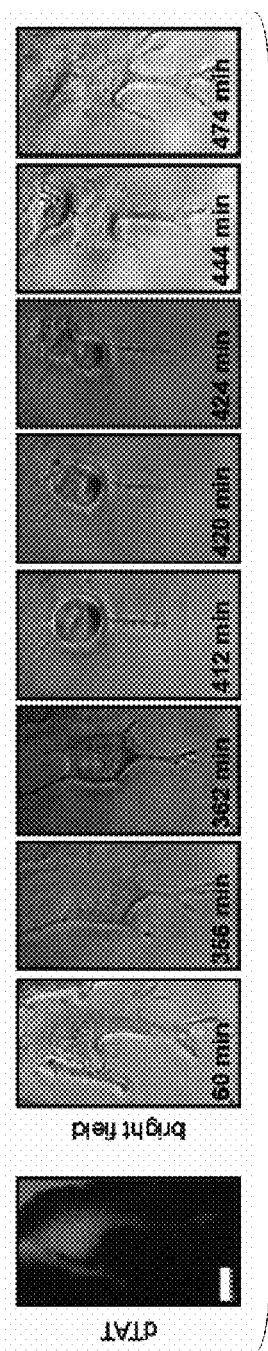
FIG. 10A  FIG. 10B  FIG. 10C  FIG. 10D

SEQUENCE LISTING

<160> NUMBER OF SEQ ID NOS: 4

<210> SEQ ID NO 1
<211> LENGTH: 9

```
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein the Xaa at positions 1, 4, 5 and 7-9 is
      Arg, "R" or any unnaturally occurring amino acid residue with
      guanidinium
<220> FEATURE:
<221> NAME/KEY: MISC_FEATURE
<222> LOCATION: (4)..(5)
<223> OTHER INFORMATION: Wherein the Xaa at positions 1, 4, 5 and 7-9 is
      Arg, "R" or any unnaturally occurring amino acid residue with
      guanidinium
<220> FEATURE:
<221> NAME/KEY: MISC_FEATURE
<222> LOCATION: (7)..(9)
<223> OTHER INFORMATION: Wherein the Xaa at positions 1, 4, 5 and 7-9 is
      Arg, "R" or any unnaturally occurring amino acid residue with
      guanidinium

<400> SEQUENCE: 1

Xaa Lys Lys Xaa Xaa Gln Xaa Xaa Xaa
1               5

<210> SEQ ID NO 2
<211> LENGTH: 39
<212> TYPE: DNA
<213> ORGANISM: Artificial Sequence
<220> FEATURE:
<223> OTHER INFORMATION: Synthetic

<400> SEQUENCE: 2
tatgggtcgt aaaaaacgtc gtcagcgtcg tcgtggtca                       39

<210> SEQ ID NO 3
<211> LENGTH: 39
<212> TYPE: DNA
<213> ORGANISM: Artificial Sequence
<220> FEATURE:
<223> OTHER INFORMATION: Synthetic

<400> SEQUENCE: 3
acccagcatt ttttgcagca gtcgcagcag caccagtat                       39

<210> SEQ ID NO 4
<211> LENGTH: 39
<212> TYPE: DNA
<213> ORGANISM: Artificial sequence
<220> FEATURE:
<223> OTHER INFORMATION: Synthetic

<400> SEQUENCE: 4
ggcattcata tggctatgag ttctttttg atcaactca                        39
```

COMPOSITIONS AND METHODS FOR THE DELIVERY OF MOLECULES INTO LIVE CELLS

CROSS-REFERENCE TO RELATED APPLICATION

This application claims the benefit of Provisional Application No. 61/876,006, filed Sep. 10, 2013, which is expressly incorporated herein by reference in its entirety.

STATEMENT OF GOVERNMENT LICENSE RIGHTS

This invention was made with U.S. Government support under NIH grant number GM087227 and grant number GM087981, awarded by the National Institutes of Health. The U.S. Government has certain rights in this invention.

STATEMENT REGARDING SEQUENCE LISTING

The sequence listing associated with this application is provided in text format in lieu of a paper copy and is hereby incorporated by reference into the specification. The name of the text file containing the sequence listing is 52683_Seq_ST25.txt. The text file is 2 KB, was created on Sep. 10, 2014, and is being submitted via EFS-Web with the filing of the specification.

FIELD OF THE INVENTION

The present disclosure relates to compositions and methods for increasing the endosomal permeability of cells without substantially adverse effects on cell viability. The methods and compositions are useful for the delivery of otherwise cell-impermeable molecules into the cells.

BACKGROUND

Protein transduction strategies are extremely useful for the investigation and manipulation of cellular processes. Proteins modified with fluorophores in vitro and delivered into live cells can, for instance, be used for imaging applications. In addition, the in cellulo determination of protein structure by nuclear magnetic resonance (NMR) has been achieved by delivering isotopically labeled proteins into live human cells. Furthermore, transcription factors that are rendered cell-permeable by tagging with cell-penetrating peptides (CPPs) or protein transduction domains (PTDs) have emerged as potential tools for ex vivo tissue regeneration applications. For instance, the transcription factors Oct4, Sox2, and Klf4 labeled with 11R or 9R reprogram fibroblasts into induced pluripotent stem cells. The transcription factor HoxB4 tagged with the PTD TAT can also be used to expand hematopoietic stems cells in vitro and potentially increase the success rate of cell transplantation procedures. These protein delivery approaches are thought to represent a safer alternative than DNA-based strategies because proteins presumably do not alter the genomic integrity of cells and because their activity is lost upon proteolysis. Cells manipulated with proteins are, therefore, less likely to give rise to cancer after transplantation into patients.

While these studies illustrate the unique opportunities provided by protein transduction technologies, current protocols are often suboptimal. PTD-proteins typically utilize the endocytic pathway as a route of cellular entry. However, the majority of PTD-proteins endocytosed by cells typically remain trapped inside endosomes. As a result, the level of protein that reaches the cytosol of cells is low and the biological outcomes achieved are poor. A possible solution to this problem is to increase the ability with which proteins escape from the endocytic pathway. This is possible with membrane-destabilizing agents that disrupt endosomes. Protocols that combine endosomolytic agents and protein of interest have therefore been examined. CPPs modified with pH-activated sequences have, for instance, been reported as additives that can improve delivery of proteins in cis or in trans. However, the hydrophobicity of the membrane-active peptide is problematic and delivery efficiency remains low. Branched multimeric CPPs have also been used in a similar manner. A branched species containing three TAT copies causes the endosomal escape of different cargos with increased efficiency. In this case however, the complicated synthetic protocols required to generate such reagents are inconvenient. Furthermore, despite improving delivery, a concern associated with these membrane active reagents is cytotoxicity. The specificity of endosomolytic agents for endosomal membranes has not been clearly characterized and lysis of the plasma membrane of cells is often observed. Furthermore, the level of endosomal leakage that can be achieved without affecting cell viability has not been established.

Despite the advances in the art, a need remains for improved methods and reagents to facilitate delivery of a wide variety of molecules and reagents to the interior of living cells with high efficiency and low impact on the viability of the target cells. Specifically, a need remains for methods and reagents to facilitate endosomal escape of molecules and reagents applied to cells with a high efficiency, low toxicity, and convenience in protocols. The present disclosure addresses this need and provides further advantages related thereto.

SUMMARY

This summary is provided to introduce a selection of concepts in a simplified form that are further described below in the Detailed Description. This summary is not intended to identify key features of the claimed subject matter, not is it intended to be used as an aid in determining the scope of the claimed subject matter.

In one aspect, the present disclosure provides a compound having the formula:

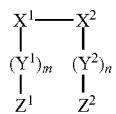

wherein:
X is a linking moiety,
Y is an amino acid residue covalently coupled to a hydrophobic moiety,
Z is a cell-penetrating peptide (CPP) moiety, wherein the CPP moiety has a net positive charge and has an amino acid sequence with 50% or more residues having a guanidinium group, and
m and n are independently 0 or 1.

In some embodiments, the CPP moiety comprises between 3 and 30 amino acids. In some embodiments, the CPP moiety comprises an amino acid sequence with at least 85% identity to the sequence set forth in SEQ ID NO:1. In some embodiments, the CPP moiety comprises the amino acid sequence set forth in SEQ ID NO:1. In some embodiments, one, two or more, or all the residues designated X in SEQ ID NO:1 are arginine residues. In some embodiments, the CPP further comprises a glycine residue at the C-terminal end. In some embodiments, the C-terminus is modified to contain an amide group. In some embodiments, the CPP of $Z^1$ and the CPP of $Z^2$ have amino acid sequences having at least 85% identity to each other.

In some embodiments, at least one of m and n is 1. In some embodiments, the hydrophobic moiety comprises a $C_6$-$C_{30}$ straight chain, branched, or cyclic group. In some embodiments, the straight chain, branched, or cyclic group includes one or more heteroatoms selected from N, O, and S. In some embodiments, the cyclic group is mono-, bi-, or tricyclic. In some embodiments, the hydrophobic moiety comprises a rhodamine group. In some embodiments, the rhodamine group is tetramethylrhodamine (TMR). In some embodiments, the amino acid residue covalently coupled to a hydrophobic moiety is lysine (K).

In other embodiments, m and n are 0, and wherein $Z^1$ and/or $Z^2$ is a CPP that comprises an amino acid residue linked to a hydrophobic moiety. In further embodiments, the amino acid residue linked to a hydrophobic moiety is the N-terminal most lysine (K) residue in the CPP amino acid sequence.

In some embodiments, X is a cysteine (C) residue. In some embodiments, $X^1$ and $X^2$ are cysteine (C) residues linked by a disulfide bond.

In some embodiments, X, Y, and/or Z are linked by amide bonds. In some embodiments, the combination of X—Y—Z comprises no more than 30 amino acid residues. In some embodiments, the compound is capable of facilitating endosomal lysis.

In another aspect, the present disclosure provides a composition having the formula:

wherein

X is a cysteine (C),

Y is an amino acid residue covalently coupled to a hydrophobic moiety,

Z is a cell-penetrating peptide (CPP) moiety, wherein the CPP moiety has a net positive charge and has an amino acid sequence with 50% or more residues having a guanidinium group, and X and Y, and Y and Z are linked by amide bonds.

In some embodiments, the compound is capable of forming a homodimer by the formation of a disulfide bond between the N-terminal cysteine (C) residues.

In some embodiments, the CPP moiety comprises an amino acid sequence with at least 85% identity to the sequence set forth in SEQ ID NO:1. In some embodiments, one, two or more, or all the residues designated X in SEQ ID NO:1 are arginine residues. In some embodiments, the CPP further comprises a glycine residue at the C-terminal end. In some embodiments, the C-terminus is modified to contain an amide group.

In some embodiments, Y is lysine (K).

In some embodiments, the hydrophobic moiety comprises a rhodamine group. In some embodiments, the rhodamine group is tetramethylrhodamine (TMR).

In another aspect, the present disclosure provides a method for enhancing endosomal permeability in a cell, the method comprising contacting a cell with a compound of the present disclosure.

In some embodiments, the cell is contacted under conditions sufficient to permit endocytosis of the compound. In some embodiments, the cell is contacted with a concentration of the compound of at least 1 µM. In some embodiments, the cell is contacted with a concentration of the compound of at least 5 µM. In some embodiments, the cell is in a culture that lacks albumin. In some embodiments, the method further comprises contacting the cell with a cell-impermeable molecule. In some embodiments, the cell is obtained from a living subject and is contacted with the compound ex vivo. In some embodiments, the cell is in a living subject and is contacted in vivo. In further embodiments, the cell is contacted in vivo by administering an amount of the compound to the subject effective to enhance the endosomal permeability of the cell. In some embodiments, the subject is a mammal.

In another aspect, the present disclosure provides a method of delivering a cell-impermeable molecule to the cytosol of a cell, the method comprising contacting a cell with a compound of the present disclosure and a cell-impermeable molecule under conditions sufficient to permit endocytosis.

In some embodiments, the cell is contacted with a concentration of the compound of at least 1 µM. In some embodiments, the cell-impermeable molecule is a peptide, a polymer including polypeptides and nucleic acids, or a small-molecule pharmaceutical. In some embodiments, the polypeptide is a transcription factor. In some embodiments, the cell-impermeable molecule is not covalently linked to the compound. In some embodiments, the cell-impermeable molecule has a net positive charge. In some embodiments, the cell is obtained from a living subject and is contacted with the compound and cell-impermeable molecule ex vivo. In some embodiments, the cell is in a living subject and is contacted with the compound and cell-impermeable molecule in vivo. In further embodiments, the cell is contacted in vivo by administering an amount of the compound to the subject effective to deliver a cell-impermeable molecule to the cytosol of the cell. In some embodiments, the subject is a mammal.

In another aspect, the present disclosure provides a method of inducing pluripotency in a cell ex vivo, the method comprising contacting a cell obtained from a subject with a compound of the present disclosure and a transcription factor under conditions sufficient to allow endocytosis, and culturing the cell to obtain pluripotency of the cell.

In some embodiments, the cell is obtained from somatic tissue in the subject. In some embodiments, the subject is a mammal. In some embodiments, the transcription factor is one of Oct4, Sox2, Klf4 and c-Myc. In some embodiments, the method further comprises subsequently administering the pluripotent cell, or a progeny cell thereof, to the subject.

In another aspect, the present disclosure provides a method of expanding a stem cell ex vivo, the method comprising contacting a stem cell with a compound of the present disclosure and a transcription factor under conditions sufficient to allow endocytosis, and culturing the cell to obtain expansion of the cell. In some embodiments, the stem cell is a hematopoietic stem cell. In some embodiments, the transcription factor is selected from the group consisting of HoxB4, HoxA4/10, Gata2, Gfl, AML1, JunB, NF-Y, Bmi1Ezh2, Dmnt3a, Cbx7, p18, p21, p27, p57, PTEN, Myc, Fbxw7, and the like.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

(FIG. 4A) Cellular localization of acTAT and dTAT in live cells. HeLa cells were incubated for 1 h with either acTAT (20 μM) or dTAT (5 μM), washed, and imaged with a 100× objective. Fluorescence images show cytosolic release for cells incubated with dTAT while acTAT shows a punctate distribution indicative of endosomal entrapment. Scale bars, 10 μm. It is noted that results similar to the punctate acTAT distribution were obtained for TAT (up to 10 μM; not shown). (FIG. 4B) dTAT fluorescence is observed in the cytosol of approximately all cells. Inverted monochrome images (black=fluorescence signal, white-no signal) of HeLa cells incubated with 5 μM dTAT for 1 h. SYTOX® blue (2 μM) was used as an indicator of cell death. Scale bars, 50 μm. (FIG. 4C) Cytosolic delivery efficiency of acTAT, TAT, and dTAT in live HeLa cells. Cells were incubated with acTAT, TAT, and dTAT (1-20 μM) for 1 h. The number of cells with detectable cytosolic and nuclear fluorescence distribution was counted and was divided by the number of total cells for each concentration tested (%) (1,000 cells/experiment, experiments were performed in triplicates, average and corresponding standard deviations represented). (FIG. 4D) dTAT overall uptake in HeLa cells responds approximately linearly to the concentration of dTAT present in the media. Cells were grown on a 48-well plate and incubated with dTAT (1-10 μM) for 1 h. Relative uptake was assessed quantitatively by measuring the bulk fluorescence of cell lysates and normalized as discussed in the methods (300,000 cells/experiment, experiments in triplicates, average/normalized and corresponding standard deviations represented).

(FIG. 8A) Effect of endocytic inhibitors on the cellular distribution of dTAT. HeLa cells were pre-treated with 50 μM amiloride or 200 nM bafilomycin for 30 and 20 min respectively, washed, and incubated with 5 μM dTAT and inhibitor. Both inhibitors blocked delivery to the cytosol and nucleus of cells. Fluorescence imaging shows a punctate distribution of TMR in the presence of bafilomycin (1,000 cells/experiment, experiments were performed in triplicates, average and corresponding standard deviations represented). Scale bar, 10 μm. (FIG. 8B) dTAT causes the cytosolic release of molecules trapped inside endosomes. A schematic illustration of the experimental steps is shown (top). First, cells were incubated with 5 μM DEAC-K9 for 1 h and washed. Inverted monochrome images show a fluorescence punctuate distribution after incubation with DEAC-K9 alone. The same cells were then incubated with 5 μM dTAT for 1 h. Images show a redistribution of DEAC-K9 to the cytosol and nucleus (inhibited by bafilomycin). Scale bars, 10 μm. (FIG. 8C) The endosomolytic activity of dTAT is highly efficient. HeLa cells expressing SNAPH2B were incubated with 5 μM dTAT and 5 μM SNAP-Surface® 488. Fluorescence images show accumulation of SNAP-Surface® 488 in the nucleus. Analysis of the green signal indicates that between 50% and 90% of SNAP-Surface® 488 escaped endosomes. Small panels show cytosolic and nuclear fluorescence of TMR. Scale bars, 10 μm.

FIGS. 10A-10D illustrate that dTAT-mediated delivery does not affect cell survival and proliferation. (FIG. 10A) dTAT does not affect cell morphology. COLO 316 cells were incubated with 5 μM dTAT for 1 h and imaged 1 and 24 h after incubation. (FIG. 10B) dTAT is not toxic to cells under conditions where efficient endosomal escape is achieved. HeLa cells were incubated with 1-10 μM dTAT for 1 h. Cell viability was assessed by a SYTOX® Green exclusion assay 1, 24, and 48 h after incubation (1,000 cells/experiment, experiments in triplicates, average and standard deviations represented). Scale bars, 10 μm. (FIG. 10C) dTAT does not affect cell proliferation. HeLa cells were incubated with 5 μM dTAT for 1 h or left untreated. Proliferation was assessed using a MTT assay for up to 36 h after incubation (150,000 cells/experiment, experiments in triplicate, average and standard deviations represented). (FIG. 10D) Cells containing cytosolic dTAT divide. HeLa cells were incubated with 5 μM dTAT for 1 h. Following incubation (t=0 h), a fluorescence image (left panel) and a time-lapse were acquired. Bright field images show a division event of a cell displaying fluorescence cytosolic distribution. Scale bars, 10 μm.

(FIG. 14A) HeLa cells expressing SNAP-H2B were incubated with 5 µM dTAT, 5 µM SNAP-Surface® 488 and 5 µM DEAC-K9. Fluorescence images (RGB and inverted monochrome) show cytosolic and nuclear localization of dTAT (fluorescence, top left panel), DEAC-K9 (fluorescence, top right panel) and SNAP-Surface® 488 (fluorescence, top middle panel). Moreover, the SNAP-Surface signal accumulated in the nucleus as shown in FIG. 8C. (FIG. 14B) HeLa cells were incubated with 5 µM dTAT, 5 µM SNAP-Surface® 488 and 5 µM DEAC-K9. Fluorescence and inverted monochrome images show cytosolic and nuclear fluorescence localization of dTAT (fluorescence, top left panel), DEAC-K9 (fluorescence, top right panel) and SNAP-Surface® 488 (fluorescence, top middle panel). Scale bars, 10 µm.

(FIG. 16A) Intact EGFP can be delivered inside live cells. HeLa cells were co-incubated with EGFP (10 µM) and dTAT (5 µM). Fluorescence images show a homogenous cytosolic distribution of EGFP. Scale bars, (100× objective: 10 µm, 20× objective: 100 µm. (FIG. 16B) dTAT-mediated delivery of TXT-Cre improves the expression of EGFP in cells containing a vector with the egfp gene upstream of a loxP-STOP-loxP sequence. HeLa transfected with the pCALNL-GFP plasmid containing an egfp gene upstream of a loxP-STOP-loxP sequence were incubated for 1 h with either TAT (5 µM) or dTAT (5 µM) in the presence of TAT-Cre (1 µM). TAT-Cre (1 µM) alone was incubated with cells as well for comparison. Addition of dTAT increased the number of EGFP+ cells (47%) (TAT-Cre alone, 2.6%) and its ability to deliver TAT-Cre inside cells surpassed that of TAT (4.8%). The number of cells in the images was approximately the same as assessed by bright field microscopy (1,000 cells/experiment, experiments in triplicate, average and standard deviations represented). Scale bars, 100 µM. (FIG. 16C) dTAT-mediated delivery of an antibody. HeLa cells were co-incubated with FITC-anti-ATP5A (20 µg/mL) and dTAT (5 µM) for 1 h at 37° C. FITC-anti-ATP5A is delivered in the cytosol of cells and stains tubular mitochondria (intense stains, more clearly visible in zoomed-in image). Scale bars, 100× objective: 10 µm, zoom-in image: 2 µm.

(FIG. 18A) Fluorescence emission spectrum of EGFP (1 µM) (donor FRET pair) (EGFP, Ex/Em 488/508 nm) excited at 488 nm. The spectrum shows an intense emission peak at around 510 nm and a small shoulder peak around 548 nm. (FIG. 18B) Fluorescence emission spectrum of a solution of EGFP (1 µM) and dTAT (5 µM) (acceptor FRET pair) (TMR, Ex/Em 556/580 nm) excited at 488 nm. The spectrum shows an intense emission peak at around 510 nm and a small shoulder peak around 548 nm. The contribution of TMR to the EGFP fluorescence spectrum (crossover fluorescence) was determined by measuring the fluorescence emission of a solution of dTAT (5 µM) excited at 488 nm (not shown). The spectrum of the solution with EGFP and dTAT is almost identical to the spectrum of EGFP alone (TMR fluorescence crossover signal was subtracted). (FIG. 18C) Fluorescence emission spectrum of ligated EGFP-CK(TMR). Using expressed protein ligation, EGFP was chemically ligated to CK(TMR) as described to produce EGFP-CK(TMR). EGFP-CK(TMR) was used a positive control for the FRET signal. Upon excitation at 488 nm, a dramatic increase in fluorescence between 560-630 nm is observed (fluorescence max approximately 580 nm), indicative of a FRET signal due the close proximity between fluorophores. This increase in fluorescence intensity was not observed in the spectrum in part b) (indicative of no interactions between EGFP and dTAT). Emission of all samples was scanned from 500 to 650 nm.

(FIG. 19A) Cells expressing TagCFP-mito (left) were imaged using the FITC and CFP filters. Tubular mitochondria were clearly observed only in the CFP channel. In a separate experiment, dTAT (5 µM) and FITC-anti-ATP5A (20 µg/mL) were incubated for 1 h with cells expressing TagCFP-mito. The inverted monochrome images show co-localization of FITC-anti-ATP5A (FITC channel) and TagCFP-mito (CFP channel). Scale bars, 2 µm. (FIG. 19B) To confirm that the mitochondrial staining is specific to FITC-anti-ATP5A, an antibody without an intracellular epitope, FITC-anti-IgG, was delivered with dTAT. FITC-anti-IgG (20 µg/mL) and dTAT (5 µM) were incubated with cells for 1 h. Inverted monochrome images show a homogenous cytosolic fluorescence distribution (top). In contrast, cells that were incubated with FITC-anti-ATP5A show fluorescence in tubular structures (bottom). Scale bars, zoom-in image: 2 µm, 100× objective: 10 µm.

(FIG. 20A) dTAT mediated delivery of HoxB4 and TAT-HoxB4 improves the expression of a luciferase reporter under a HoxB4-dependent promoter. NIH 3T3 transfected with a luciferase reporter were incubated for 1.5 h with either HoxB4 or TAT-HoxB4 (200 nM) in presence or absence of dTAT (3 µM). Addition of dTAT results in a 53.1 and 307.4 fold increase in the luciferase induction obtained with Hoxb4 and TAT-Hoxb4, respectively. Incubation with TAT-mCherry (200 nM) and/or dTAT (3 μM) serves as negative controls (400,000 cells/experiment, experiments in duplicate, average and standard deviations represented). (FIG. 20B) The amount of DEAC-K9 delivered in the cytosol and nucleus of live cells can be titrated. HeLa cells were incubated with dTAT (5 μM) and increasing amounts of DEAC-K9 (1, 2.5, 5, 10, 20 μM). The fluorescence intensity of cells displaying cytosolic release was assessed by microscopy (fluorescence signal display using pseudocolor, colorscale: blue=lowest intensity, red=highest intensity) and compared to the bulk fluorescence of cell lysates. In both analyses, the fluorescence intensity of cells responds linearly to the concentration of DEAC-K9 in the media. (Microscope: 1,000 cells/experiment, fluorometer: 300,000 cells/experiment; experiments in triplicate, average and standard deviations represented). Scale bars, 10 μm. (FIG. 20C) Induction of luciferase expression by dTAT-mediated delivery of HoxB4 can be controlled. NIH 3T3 cells were co-incubated with HoxB4 (25-200 nM) and dTAT (3 μM) and luciferase induction was measured as described in (a) (400,000 cells/experiment, experiments in duplicates, average and standard deviations represented).

DETAILED DESCRIPTION

Figure 1:
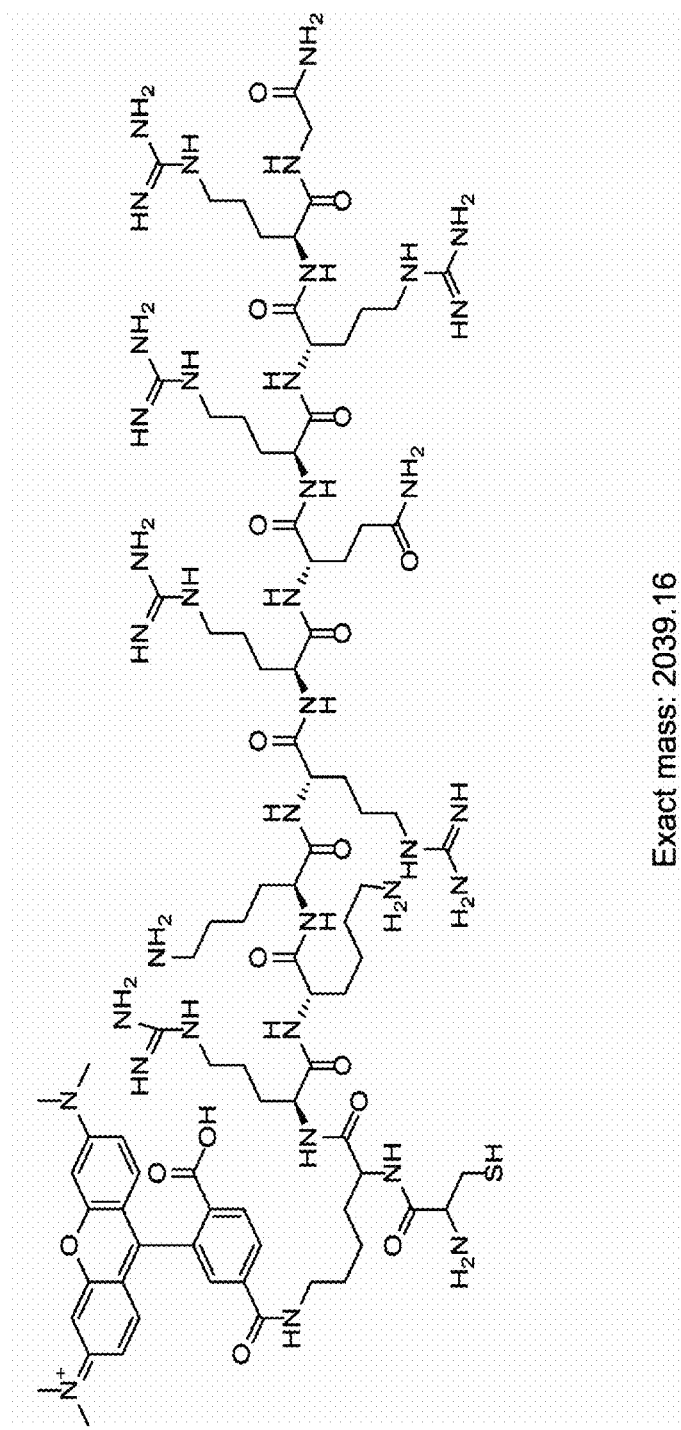
FIG. 1 illustrates the structure and expected mass of the TAT construct.

Macromolecular delivery strategies typically utilize the endocytic pathway as a route of cellular entry. However, endosomal entrapment severely limits the efficiency with which macromolecules penetrate the cytosolic space of cells. Strategies to enhance endosomal escape often lead to increased cytotoxicity because of lack of specificity of endosomolytic agents for the endosomal membrane. This disclosure describes the surprising discovery that the dimerization of a cell penetrating peptide (CPP), such as a domain of the HIV transactivating transcriptional activator, or trans-activator of transcription (referred to herein as "TAT CPP domain"), penetrates live cells by escaping from endosomes with a particularly high efficiency. As used herein, the terms cell-penetrating peptide (CCP) and protein transduction domain (PTD)) can be used interchangeably as peptides that promote cellular uptake of various molecular cargo, thus, the terms refer to peptides that can promote intracellular delivery of various cis or trans cargo. By mediating endosomal leakage, the CPP dimer facilitates the delivery of small molecules, peptides, and proteins into cultured cells after a simple co-incubation procedure. As described in more detail below, incorporation of two TAT CCP domains into a dimer compound resulted in a novel reagent (dTAT) that facilitated delivery proteins and small molecules into live cells with extreme efficiency and without negatively affecting cell viability and proliferation. Additional surprising advantages related to the novel dTAT compound are also described. For example, cytosolic delivery was achieved in most cells in a culture, in several different cell lines, and with only a relatively small amount of material remaining trapped inside intact endosomes. Delivery did not require binding interactions between dTAT and the target cargo, multiple molecule species were able to be delivered at once, and delivery could be repeated in the same cells. Remarkably, dTAT-mediated delivery did not noticeably impact cell viability and proliferation. dTAT-mediated delivery was further evaluated with HoxB4, a transcription factor with therapeutic potential for in vitro expansion of hematopoietic stem cells. Specifically, addition of dTAT to the incubation media augmented the induction of a luciferase reporter 24-fold over that obtained by treatment with HoxB4 alone and 61-fold over that obtained with TAT-HoxB4 (a protein construct fused to TAT) alone. Finally, the transcriptional activity of HoxB4 can also be precisely controlled by simply changing the amount of protein administered extracellularly. Overall, as described herein, the inventors demonstrated that this new delivery strategy based on the novel CPP dimers, such as the novel dTAT reagents, is extremely useful for cell-based assays, cellular imaging applications, ex vivo manipulation and reprogramming of cells, and in vivo administrations of therapeutic agents, among other applications.

In accordance with the foregoing, in one aspect, the disclosure provides a compound having Formula (I):

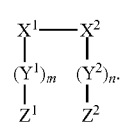

Formula (I)

In the compound represented by Formula (I), X is a linking moiety, Y is an amino acid residue covalently coupled to a hydrophobic moiety, and Z is a cell-penetrating peptide (CPP) moiety. It will be understood that the superscript designations (i.e., $^1$ and $^2$) indicate that the various subcomponents designated thereby are not required to be identical, but can optionally encompass variations. For example, $Z^1$ and $Z^2$ can be the identical or different CPP moieties so long as each satisfies the requirements of a CPP moiety. Any description provided herein with reference to a subcomponent without a designated superscript refers to the general category of subcomponents and can apply specifically to either one or both specific subcomponents in the compound. The subscript designations m and n are independently 0 or 1, which indicate absence or presence of the specific subcomponent, respectively. In some embodiments, at least one of m and n is 1. In some embodiments, only one of m and n is 1. In some embodiments, both m and n are 1. In some specific embodiments, described in more detail below, both m and n are 0. In any embodiment wherein m and/or n is 0, it will be understood that the corresponding X and Z subcomponents are directly linked without any intervening Y subcomponent. The compound described herein can be referred to herein alternately as the dimer compound, the endosomolytic compound, or a compound of the present disclosure.

In some embodiments, the cell-penetrating peptide (CCP) moiety has between 3 and 30 amino acids.

As used herein, a "peptide" or "polypeptide" refers to polymers of two or more amino acids joined together by an amide bond (that is, a "peptide bond"). Peptides typically comprise up to or include 50 amino acids and can be linear or cyclic. As used herein, an "amino acid" refers to any of the 20 naturally occurring amino acids found in proteins, D-stereoisomers of the naturally occurring amino acids (e.g., D-threonine), unnatural amino acids (e.g., synthetic amino acids with variant side chains as compared to the naturally occurring amino acids), and chemically modified amino acids. Each of these types of amino acids is not mutually exclusive. α-Amino acids comprise a carbon atom to which is bonded an amino group, a carboxyl group, a hydrogen atom, and a distinctive group referred to as a "side chain." The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine).

The following abbreviations are used for the 20 naturally occurring amino acids: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Amino acids, and, more specifically, their side chains, are well-known and can be characterized by their chemical characteristic(s). For example, amino acid side chains may be positively charged, negatively charged, or neutral. The pH of a solution affects the charged nature of certain side chains, as is known by those of skill in the art. Non-limiting examples of side chains that may be positively charged include histidine, arginine, and lysine. Non-limiting examples of side chains that may be negatively charged include aspartic acid and glutamic acid. Non-limiting examples of side chains that may be characterized as neutral include glycine, alanine, phenylalanine, valine, leucine, isoleucine, cysteine, asparagine, glutamine, serine, threonine, tyrosine, methionine, proline, and tryptophan.

Amino acids may be also characterized by the polarity of their side chains. Polar side chains, which are typically more hydrophilic than non-polar side chains, include, for example, those of serine, threonine, tyrosine, cysteine, asparagine, and glutamine. Non-polar side chains, which are typically more hydrophobic than polar side chains, include, for example, those of glycine, alanine, valine, leucine, isoleucine, proline, methionine, phenylalanine, and tryptophan. One may determine polarity of a side chain using conventional techniques known in the art involving atom electronegativity determinations and three-dimensional structural assessments of side chains. One may also compare hydrophobicities/hydrophilicities of side chains using conventional techniques known in the art, such as comparing the octanol/water partition coefficient of each amino acid.

As used herein, a "chemically modified amino acid" refers to an amino acid whose side chain has been chemically modified. For example, a side chain may be modified to comprise a signaling moiety, such as a fluorophore or a radiolabel. A side chain may be modified to comprise a new functional group, such as a thiol, carboxylic acid, or amino group. Post-translationally modified amino acids are also included in the definition of chemically modified amino acids.

In some embodiments, the CPP has a net positive charge.

In some embodiments, the CPP has an amino acid sequence with 50% or more of the amino acid residues having a guanidinium group in the side chain. For example, the amino acid sequence can have 50%, 55%, 60%, 65%, 70%, 75%, 80%, 85%, 90%, 95%, or all of its amino acids, or any derivable range therein, having a guanidinium group in the side chain. A guanidinium group is represented by Formula (II):

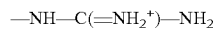

Formula (II).

In some embodiments, one or more of the amino acids having a guanidinium group is an arginine (Arg; R) residue. As is understood in the art, an Arg residue has a side chain with a 3-carbon aliphatic straight chain, the distal end of which is capped with a guanidinium group. In some embodiments, one or more of the amino acids having a guanidinium group is an analogue of Arg, wherein the side chain is modified or synthetically different in some manner. Such modifications can include the addition or deletion of carbons in the side-chain, relative to the naturally occurring Arg, resulting in a longer or shorter side chain that is capped with a guanidinium group. In addition, the side chain can be modified to contain branch structures or other functional groups. In some embodiments, the guanidinium group can be present in a branch structure. In some embodiments, the amino acid residue can comprise more than one guanidinium group. The generation of Arg analogs can be accomplished according to known techniques that include introducing the intended modifications to naturally occurring Arg and generating synthetic amino acids de novo that contain one or more guanidinium groups.

In some embodiments, the CPP moiety, as represented by Z in Formula (I), comprises an amino acid sequence with at least 85%, 90%, 95%, 96%, 97%, 98%, 99%, or any range or percentage included therein, identity to the sequence XKKXXQXXX (SEQ ID NO:1). It is noted that each designation X that appears in SEQ ID NO:1 independently refers to an arginine (Arg; R) or an unnaturally occurring residue with a guanidinium group, as described above. In some embodiments, the CPP comprises the amino acid sequence set forth in SEQ ID NO:1. In some embodiments, the CPP comprises or consists of the amino acid set forth in SEQ ID NO:1 with an additional glycine at the (C-terminal end. In some embodiments, the CPP moiety consists of the amino acid sequence set forth in SEQ ID NO: 1. In any of these embodiments, one, two or more, or all of the X designations in SEQ ID NO:1 refer to arginine (Arg; R) residues. In some embodiments, the CPP sequence of $Z^1$ and the CPP sequence of $Z^2$ have amino acid sequences that are at least 85%, 90%, 95%, 96%, 97%, 98%, 99%, 100% or any range or percentage included therein, identical to each other.

As used herein, the terms indicating "percent identity" or "percent identical" refer to the percentage of amino acid residues in a polypeptide sequence that are identical with the amino acid sequence of a specified molecule (such as SEQ ID NO:1) after aligning the candidate and subject sequences to achieve the maximum percent identity. For example, percentage identity between two protein sequences can be determined by pairwise comparison of the two sequences using the bl2seq interface at the Web site of the National Center for Biotechnology Information (NCBI), U.S. National Library of Medicine, 8600 Rockville Pike, Bethesda, Md. 20894, U.S.A. The bl2seq interface permits sequence alignment using the BLAST tool described by Tatiana, A., et al., "Blast 2 Sequences—A New Tool for Comparing Protein and Nucleotide Sequences," *FEMS Microbiol. Lett.* 174:247-250 (1999). The following alignment parameters can be used: Matrix=BLOSUM62; Gap open penalty=11; Gap extension penalty=1; Gap x_dropff=50; Expect=10.0; Word size=3; and Filter=off.

As indicated above, in some embodiments of the compound represented by Formula (I), at least one of m and n is 1. Accordingly, in some embodiments, the compound comprises at least one amino acid residue covalently coupled to a hydrophobic moiety, as represented by Y in Formula (I). Without being bound to any particular theory, it is believed that the presence of one or more hydrophobic moieties at position(s) Y in the dimer compound create a lipophilic wall-head at the amino terminal of the CPP domain(s). This wall-head likely leads to a higher affinity of the overall dimer compound for the endosome membrane and facilitates the endosomolytic activity of CCP domains in the dimer compound.

In some embodiments, the hydrophobic moiety comprises between 6 and 40 carbon atoms. In some embodiments, the hydrophobic moiety comprises a straight chain, branched, or cyclic group. In some embodiments, the cyclic group is or comprises a monocyclic, bicyclic, or tricyclic group.

In some embodiments, the hydrophobic moiety further comprises one or more heteroatoms selected from nitrogen (N), oxygen (O), and sulfur (S).

Exemplary, non-limiting hydrophobic moieties include: aromatic molecules (for example, xanthenes, anthracene, indoles, and the like), amino acids (for example, histidine, tryptophan, phenylalanine, tyrosine residues, and the like), fluorophores, lipophilic molecules, aliphatic molecules (for example, fatty acids and the like), and the like. In some embodiments, the hydrophobic moiety is lipophilic.

In specific embodiments, the hydrophobic moiety comprises a rhodamine group, or derivative thereof. Rhodamine groups comprise a family of related chemical compounds that are commonly used as dyes due to their ability to fluoresce. The core rhodamine structure is represented by Formula (III):

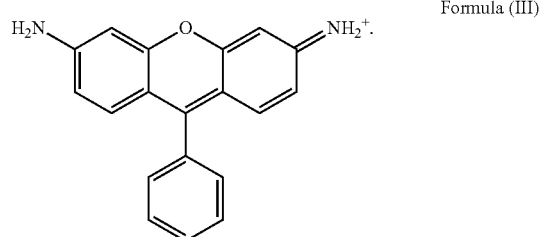

Formula (III)

Rhodamine and its derivatives are generally known to be soluble in water because of its positive charge (many derivatives are provided in salt form). Notwithstanding this solubility, rhodamine and its derivatives are included herein as a type, or part, of a "hydrophobic moiety" because of hydrophobic and lipophilic properties imparted to these compounds by the aromatic core.

In some embodiments, the hydrophobic moiety comprises a rhodamine derivative. In some embodiments, the rhodamine derivative is tetramethylrhodamine (TMR), represented by Formula (IV):

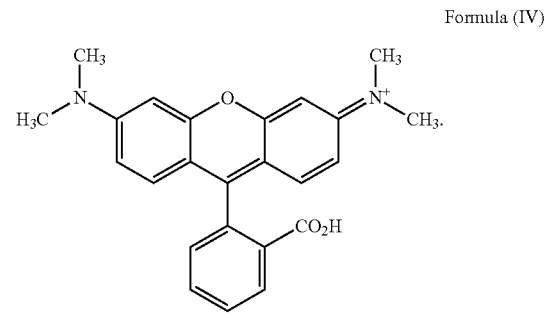 [SMILES: CN(C)c1ccc2c(-c3ccccc3C(=O)O)c3ccc(=[N+](C)C)cc-3oc2c1]

Formula (IV)

In some embodiments, the TMR is a 5(6)-carboxy TMR to facilitate attachment to an amino acid residue of the compound. The amino acid residue covalently coupled to a hydrophobic moiety can be any of the above described amino acids amenable to such coupling. In some embodiments, such as described in more detail below, the amino acid is a lysine (Lys; K).

As described above, in certain specific embodiments, both m and n are 0. In such embodiments, the compound still comprises at least one hydrophobic moiety as described herein. However, instead of being covalently coupled to an amino acid that is distinct from the amino acids of the CPP, the at least one hydrophobic moiety is covalently coupled to at least one of the amino acids within at least one of the two CPP sequences. In these embodiments, it is preferable that the at least one amino acid (coupled to the hydrophobic moiety) is located at a position within at least one CPP sequence that is closer to the terminus that is proximal to (i.e., bound to) the X subcomponent of the compound, as compared to the terminus that is not proximal to (i.e., not bound to) the X subcomponent of the compound. In some embodiments, the at least one amino acid (coupled to the hydrophobic moiety) is located at a position within the CPP sequence that is the terminal position or within 1, 2, 3, 4, or 5 amino acid residue positions of the terminal position that is proximal (i.e., bound to) the X subcomponent of the compound. In some embodiments, the at least one amino acid (coupled to the hydrophobic moiety) is the N-terminal-most lysine residue in the CPP amino acid sequence.

Linking moieties, as represented in Formula (I) by X, can be any chemical moieties that can facilitate a stable linkage useful to join two monomer units that each comprise a CPP moiety and hydrophobic moiety, as described herein. In some embodiments, $X^1$-$X^2$ as represented in Formula (I) represents a single linking structure. In some embodiments, $X^1$ and $X^2$ each represent a distinct, and optionally different, moiety that in combination are capable of forming a stable linkage between the two monomer units. In some embodiments, the stable linkage can be one or more covalent bonds between a plurality of subcomponents. In other embodiments, the stable linkage can be an ionic bond.

An illustrative, non-limiting example of linking moieties as represented by X in Formula (I) is the amino acid residue cysteine (Cys; C), which is capable of forming a disulfide bond with another cysteine residue. Thus, in one embodiment, $X^1$ and $X^2$ are both cysteine residues, which are mutually linked by a disulfide bond. In another illustrative example, one of $X^1$ and $X^2$ is a biotin molecule, and the other of $X^1$ and $X^2$ is a moiety that specifically binds to biotin, such as avidin, streptavidin, neutravidin, and the like. As is readily understood in the art, biotin and its specific binding partner, such as avidin, streptavidin, neutravidin, and the like, form a strong, non-covalent bond that approaches the strength of a covalent bond.

Figure 2:
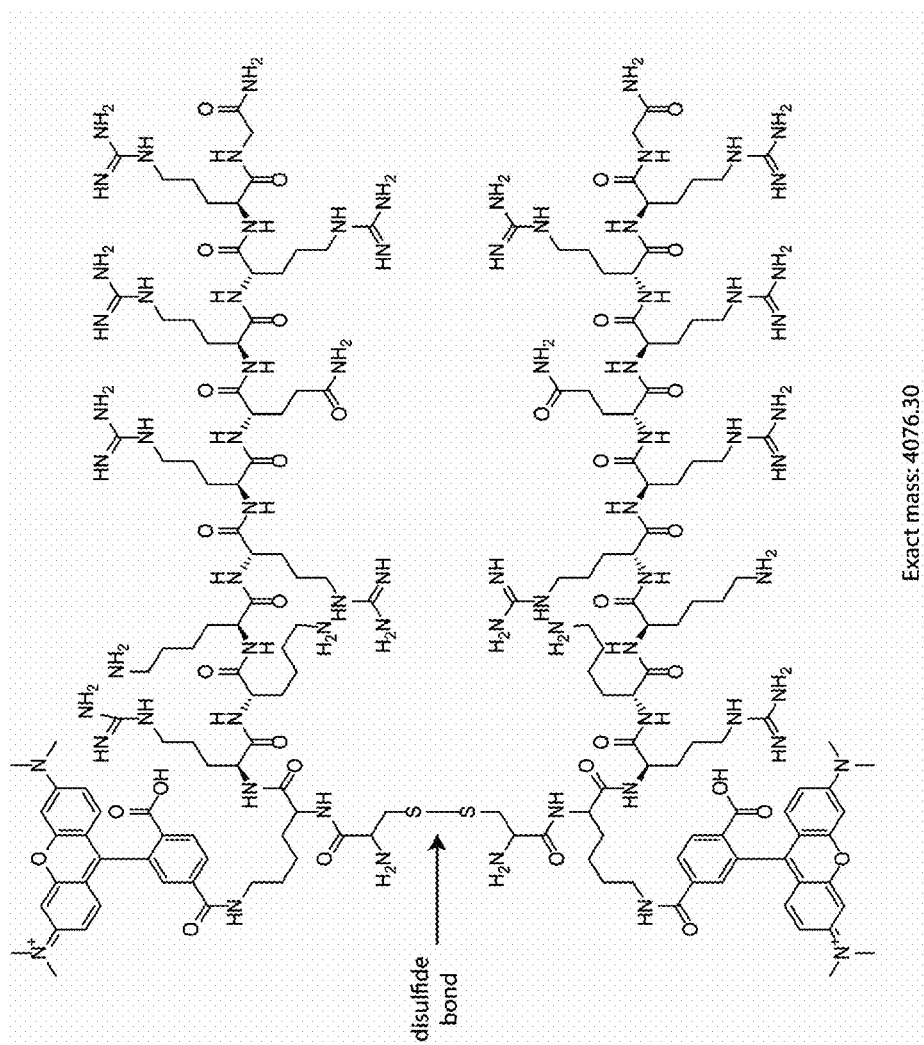
FIG. 2 illustrates the structure and expected mass of a dTAT construct incorporating a disulfide bond linkage (indicated with an arrow).

It will be appreciated that the linkage between the monomer units provided by the linking moieties does not need to be permanent. Instead, the linkage should be sufficiently stable to maintain the overall dimer structure during endosomal capture and endosomal escape into the cytosol. Thereafter, the linkage may no longer be required, and in some cases is preferably broken to preserve cell viability. For example, as described below, an exemplary dTAT dimer construct is maintained by a disulfide bond between two monomer units. See FIG. 2 In this embodiment, the disulfide bond can be cleaved within the cytosol, resulting in monomer units that have relatively reduced (or no) membrane disruption activity thereafter.

Figure 21:
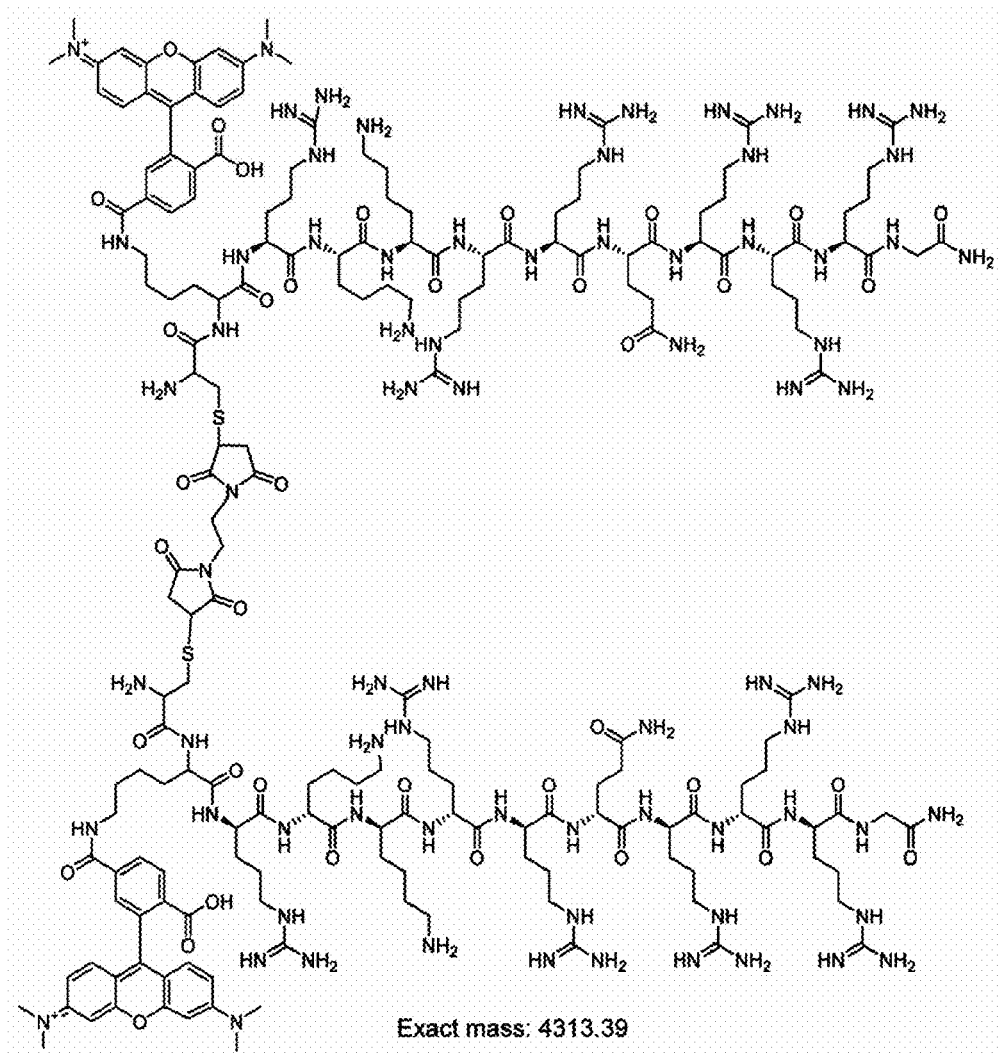
FIG. 21 illustrates the structure and expected mass of a "non-reducible dTAT dimer" (nrdTAT) construct.

Alternatively, the linkage between the monomer units can be a non-reducible linkage. An exemplary construct with a non-reducible linkage between two TAT monomers is illustrated in FIG. 21 and was shown to retain the cell-permeating functionality of dTAT, as described in more detail below. This demonstrates that the specific linkage supporting a dTAT dimer construct can be modified or replaced without adversely affecting functionality.

In some embodiments, the compound subcomponents X, Y, and/or Z as represented in Formula (I) (e.g., $X^1$, $Y^1$, and/or $Z^1$) are linked by amide bonds. For example, in some embodiments, each of $X^1$, $Y^1$, and/or $Z^1$ (and/or $X^2$, $Y^2$, and/or $Z^2$) comprise at least one amino acid, wherein the at least one amino acid from each of $X^1$, $Y^1$, and/or $Z^1$ (and/or $X^2$, $Y^2$, and/or $Z^2$) are linked by amide bonds. In some embodiments, only two of $X^1$, $Y^1$, and $Z^1$ (and/or $X^2$, $Y^2$, and $Z^2$) are linked by amide bonds. In some embodiments, all of $X^1$, $Y^1$, and $Z^1$ (and/or $X^2$, $Y^2$, and $Z^2$) are linked by amide bonds. In some embodiments, the X, Y, and/or Z subcomponents represented in Formula (I) (e.g., $X^1$, $Y^1$, and/or $Z^1$) are indirectly linked by intervening subcomponents. The subcomponents can be intervening amino acids and, thus, can be linked to the X, Y, and/or Z subcomponents by amide bonds.

In some embodiments, the combination of X—Y—Z as a monomer subunit of the compound represented in Formula (I), i.e., $X^1$—$Y^1$—$Z^1$ and/or $X^2$—$Y^2$—$Z^2$, comprises 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35 amino acid residues.

As described in more detail below, administration of sufficient concentration of monomeric TAT (TAT), as illustrated in FIG. 1 and as represented in the context of Formula (I) by the monomer X—Y—Z, is administered in sufficient concentrations to cells, resulting in some cytosolic fluorescence. This indicates that in sufficient concentration, the TAT monomeric compound is capable of some degree of self-dimerization during endocytosis. A monomer that can self-assemble inside endosomes during endosomal capture provides several potential benefits, such as further reducing non-specific membrane interaction by only dimerizing into the membrane-active compound upon endocytosis.

Accordingly, in another aspect, the present disclosure provides a compound having the formula X—Y—Z, wherein X is a cysteine residue, Y is an amino acid residue covalently coupled to a hydrophobic moiety, and Z is a cell-penetrating peptide (CPP) moiety. The CPP moiety has a net positive charge and has an amino acid sequence with 50% or more residues having a guanidinium group. Preferably, the X and Y subcomponents, and the Y and Z subcomponents are linked by amide bonds. As with the compound of the above aspect, the compound described herein can be referred to alternately as the monomer compound, the endosomolytic compound, or a compound of the present disclosure.

The compound of this aspect is capable of forming a homodimer by the formation of a disulfide bond between the N-terminal cysteine residues of two compounds.

The CPP is described above. In some embodiments, the cell-penetrating peptide (CCP) moiety has between 3 and 30 amino acids. In specific embodiments, the residues having a guanidinium group can independently be an arginine (Arg; R) amino acid residue, or a synthetic, unnaturally occurring amino acid such as a synthetic Arg analogue.

In some embodiments, the CPP has an amino acid sequence with at least 85%, 90%, 95%, 96%, 97%, 98%, 99%, or any range or percentage included therein, identity to SEQ ID NO:1, described above. In some embodiments the CPP comprises the amino acid sequence set forth in SEQ ID NO:1. In some embodiments, the CPP comprises or consists of the amino acid set forth in SEQ ID NO:1 with an additional glycine at the C-terminal end. In some embodiments, the CPP moiety consists of the amino acid sequence set forth in SEQ ID NO:1.

In some embodiments, Y is a lysine residue (Lys; K).

The hydrophobic moiety is described above. In some specific embodiments, the hydrophobic moiety comprises a C6-C30 straight chain, branched, or cyclic group. In some embodiments, the cyclic group is or comprises a monocyclic, bicyclic, or tricyclic group. In some embodiments, the hydrophobic moiety further comprises one or more heteroatoms selected from nitrogen (N), oxygen (O), and sulfur (S). In some embodiments, the hydrophobic moiety comprises a rhodamine or rhodamine derivative. In some embodiments, the rhodamine derivative is tetramethylrhodamine (TMR), represented by Formula (IV).

In some embodiments, the combination of X—Y—Z comprises 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35 amino acid residues. In some embodiments, the X, Y, and/or Z subcomponents represented are indirectly linked by intervening subcomponents. The subcomponents can be intervening amino acids and, thus, can be linked to the X, Y, and/or Z subcomponents by amide bonds.

In another aspect, the present disclosure provides a method of enhancing endosomal permeability in a cell, the method comprising contacting a cell with a compound of the disclosure, as described herein above.

In this aspect, the cell is contacted under conditions sufficient to permit endocytosis of a cell-impermeable molecule. For example, the cell can be maintained in culture conditions known in the art that are conducive to cell viability and, thus, sufficient for the cell to maintain an operable endocytic pathway. In some embodiments, the cell is cultured in vitro. In further embodiments, the cell is cultured in vivo in media that lacks albumin, which can, in certain instances, reduce activity of the described compounds. In other embodiments, the cell is obtained from a living subject and is contacted ex vivo. In such embodiments, known culturing techniques can be applied to maintain the cell ex vivo for a period of time. In some embodiments, as described below, the cell is in vivo in a living subject and the endosomolytic compound is administered to the subject.

In some embodiments, the cell is contacted with a concentration of the endosomolytic compound of at least 0.1 µM, 0.5 µM, 1 µM, 2 µM, 3 µM, 4 µM, 5 µM, or higher. The term concentration can be determined with regard to the volume of the local environment for the cell. For example, the concentration can be determined in terms of the volume of the cell culture media in contact with the cell.

In some embodiments, the method further comprises contacting the cell with a cell-impermeable molecule. Cell-impermeable molecules are chemical agents that do not normally cross a cell membrane unaided and preferably elicit an intended effect on the cell upon or after being introduced into the cytosol. The only theoretical limitation is that the molecules must be capable of being endocytosed, which imposes certain size limitations. Illustrative, non-limiting examples of cell-impermeable molecules include peptides, polypeptides, proteins (e.g., polypeptides exceeding about 50 amino acids), nucleic acids, other polymers, pharmaceutical compositions, and the like. In some embodiments, the polypeptides or proteins are transcription factors. Exemplary transcription factors are discussed in more detail below.

In some embodiments, the cell-impermeable molecule is linked or conjugated to the compound, covalently or otherwise. However, in other embodiments, the cell-impermeable molecule is not linked or conjugated to the compound. For example, as described in more detail below, various cell-impermeable molecules including transcription factors and dyes that were not linked to dTAT were successfully delivered into the cytosol of various cells when administered coordinately with dTAT, but not linked or conjugated thereto. One potential advantage is that this allows the concentration or amount of the "cargo" cell-impermeable molecule to be easily adjusted independently of the endosomolytic compound of the present disclosure.

As described below, the dTAT compound has a net positive charge. It is theorized that absent opposite charges, the cell-impermeable molecule will not interact with the endosomolytic compound (such as dTAT described below), thus avoiding interfering with its endosomolytic properties. Accordingly, in some embodiments, the cell-impermeable molecule has a net positive charge. However, in other embodiments, the cell-impermeable molecule can have a net negative charge. In these embodiments, the cell-impermeable molecule can be contacted to the cell with additional, commonly known reagents that effectively shield the negative charge of the cell-impermeable molecule. This charge shielding avoids detrimental interaction, if any, between the cell-impermeable molecule and the compound of the disclosure. For example, it is known that chemicals such as calcium phosphate and DEAE-dextran or cationic lipid-based reagents can be used to create a more electrostatically neutral environment around a DNA molecule and, thus, ameliorate the effects of the DNA's negative charge. An exemplary cationic lipid is Lipofectamine™ (Invitrogen/Life Technologies, CA, USA).

Figure 14A:
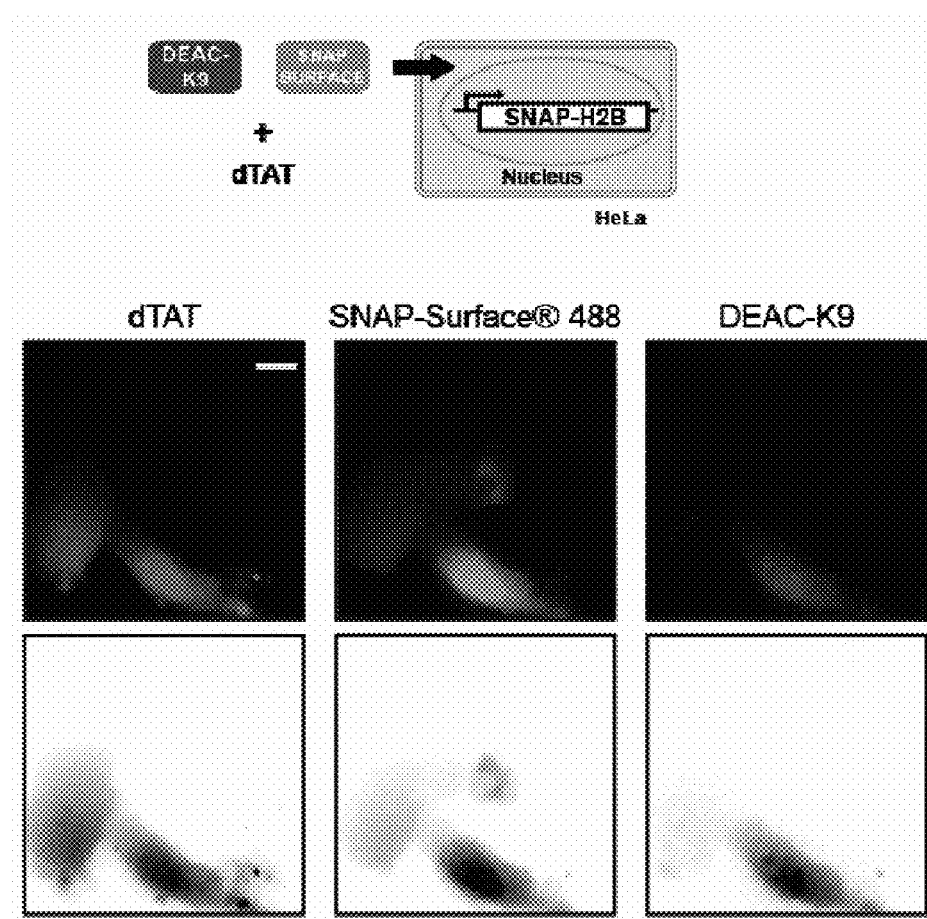
FIGS. 14A-14B illustrate that dTAT mediates delivery of two cargos simultaneously inside live cells.
Figure 14B:
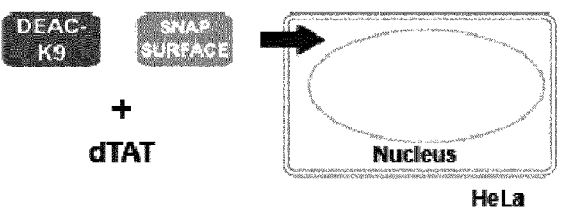
Figure 14B:
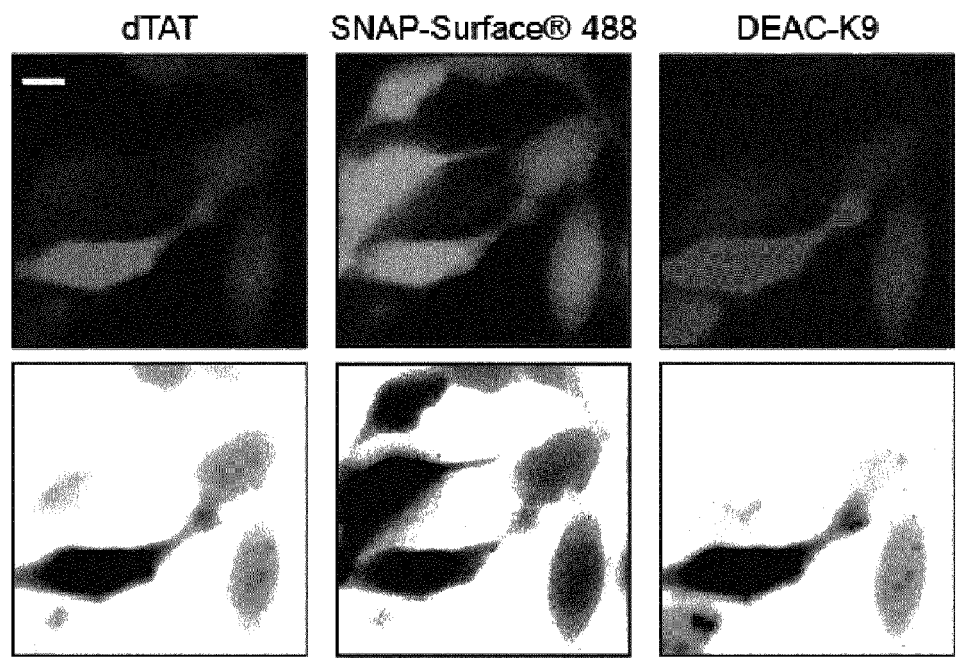

As demonstrated below and illustrated in FIG. 14, the dTAT compound facilitated simultaneous delivery of DEAC-K9 and SNAP-Surface® 488. Accordingly, in some embodiments, the method comprises contacting the cell with a plurality of different cell-impermeable molecules.

As demonstrated below, administrations of the endosomolytic agent and cell-impermeable molecule can be repeated multiple times without detriment to cell viability. Accordingly, in some embodiments, the method further comprises contacting the cell with the endosomolytic compound and one or more cell-impermeable molecules at a time subsequent to the first instance of contacting the cell with the endosomolytic compound and one or more cell-impermeable molecules. In some embodiments, the contacting step is repeated 1, 2, 3, 4, 5 or more times, each time potentially with the same or different cell-impermeable molecule.

In some embodiments, the cell is obtained from a living subject and is contacted ex vivo with the endosomolytic compound of the disclosure and the cell-impermeable molecule. For example, a cell obtained from a subject can be contacted ex vivo with the compound and an agent, such as any transcription factor known to facilitate pluripotency. Once the requisite degree of pluripotency is achieved, the cell, or progeny thereof, can be administered back into the subject or another subject in need thereof. In another embodiment, the cell, or progeny thereof, are further differentiated according to known methods that can include additional contacting with the compound of the present disclosure. The differentiated cell(s) can then be administered back to the subject or a different individual in need thereof.

As indicated above, some embodiments of the method encompass contacting a cell in vivo with the endosomolytic compound of the present disclosure. In further embodiments, the cell is also contacted with an effective amount of a cell-impermeable molecule that addresses a therapeutic need. In some embodiments, the endosomolytic compound and/or the cell-impermeable molecule is targeted to one or more specific cells or cell types in the body of the subject. This can be accomplished using various well-recognized delivery vehicles such as liposomes, nanoparticles, virus like particles (VLPs), and the like, that are engineered to specifically target cells of interest. For example, the cell can be an aberrant or cancerous cell with a known surface receptor amenable to particle targeting. The particle can deliver the endosomolytic compound (along with a cell-impermeable agent) that causes the death of the cell. In another example, the cell is a stem cell that is targeted with the endosomolytic compound (along with a cell-impermeable agent) that induces differentiation of the stem cell into a needed progeny cell, for example, to regenerate tissue or a cell population.

The subject can be any animal, such as mammal, reptile, arthropod, mollusk, and the like. In some embodiments, the mammalian subject is a primate (including a monkey, an ape, and a human), a rodent (including a mouse, a rat, a guinea pig, and the like), a cat, a dog, a cow, a horse, a sheep, a goat, a pig, and the like.

Accordingly, in a related aspect, the present disclosure also provides a method of delivering a cell-impermeable molecule to the cytosol of a cell, the method comprising contacting a cell with an endosomolytic compound, as described hereinabove, and a cell-impermeable molecule under conditions sufficient to permit endocytosis.

In another aspect, the present disclosure provides a method of inducing pluripotency in a cell ex vivo. The method comprises i) contacting a cell obtained from a subject with an endosomolytic compound, as described hereinabove, and a transcription factor under conditions sufficient to allow endocytosis, and ii) culturing the cell to obtain pluripotency of the cell.

As used herein, the terms "pluripotent" and "pluripotency" are used to refer to the capacity or potential of a cell to develop into a plurality of different cell types. As used, the term is intended to include all categories of stem cells, such as totipotent cells, pluripotent cells, multipotent cells (including mesenchymal cells), and oligopotent cells. It will be appreciated that many techniques are known to induce pluripotency from somatic cells through genetic manipulations to obtain cells that are useful precursors to a different cell-types of interest.

Illustrative, non-limiting examples of known transcription factors that are useful in this aspect to promote pluripotency include Oct4, Sox2, Klf4, c-Myc, and the like.

The method of this aspect provides the advantage of inducing pluripotency by efficient delivery of the appropriate transcription factors without detrimental effects on the cells. As described, delivery can be repeated and can be applied to a plurality of different cell-impermeable molecules. Pluripotent cells can then be administered back into the source subject or another subject in need thereof. In alternative embodiments, the pluripotent cells are further differentiated into any preferred cell types. Methods to differentiate pluripotent cells in ex vivo cultures are known in the art, and can include further administrations of an endosomolytic compound of the present disclosure. The differentiated cells can be maintained in culture and/or can be administered back into the source subject or another subject, such as for appropriate therapeutic or research purposes.

In another aspect, the present disclosure provides a method of expanding a stem cell ex vivo. The method comprises i) contacting a stem cell with an endosomolytic compound of the present disclosure and a transcription factor under conditions sufficient to allow endocytosis, and ii) culturing the cell to obtain expansion of the cell.

As used herein, the term "expanding a stem cell" refers to propagating a cell population from an initial feeder stem cell or cells, wherein the members of the expanded population retain characteristics of the initial feeder cell or cells, such as a requisite degree of pluripotency. Expansion techniques include providing an appropriate culture environment for cell growth and division. This environment can include a combination of media, supplements, growth scaffolds and reagents and may or may not involve the need for healthy feeder populations or conditioned media. Expanded stem cells are beneficial or useful therapeutically as drug screening tools for core research purposes, and the like. For example, expanded hematopoietic stem cells can be administered to a subject that has had ablative bone marrow cancer therapy in an effort to repopulate the bone marrow and blood with various lineages of blood cells.

In some embodiments, the stem cell is a hematopoietic stem cell.

In some embodiments, the transcription factor HoxB4, HoxA4/10, Gata2, Gf1, AML1, JunB, NF-Y, Bmi1Ezh2, Dmnt3a, Cbx7, p18, p21, p27, p57, PTEN, Myc, Fbxw7, and the like.

It will be understood that any embodiment, characteristic, element, definition, or general description provided for any aspect of the disclosure can be applied to any other aspect of the disclosure without limitation, unless explicitly stated. Thus, any embodiment discussed herein can be implemented with respect to any method, agent, or composition of the invention, and vice versa. Furthermore, agents and compositions of the invention can be used to achieve methods of the invention.

The use of the word "a" or "an," when used in conjunction with the term "comprising" herein can mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

As an alternative to or in addition to "comprising," any embodiment herein can recite "consisting of." The transitional phrase "consisting of" excludes any element, step, or ingredient not specified in the claim.

Publications and references cited herein, and the material for which they are cited, are hereby specifically incorporated by reference in their entireties.

The following is a description of the discovery that novel TAT dimers (dTAT) surprisingly mediate endosomal leakage and facilitate efficient delivery of small molecules, peptides, and proteins into cultured cells by a simple co-incubation procedure. dTAT was formed by creation of a disulfide bridge between two TAT peptides. Cytosolic delivery was achieved without impacting cell viability or proliferation. Multiple molecules were delivered simultaneously, and delivery to the same cells was amenable to repetition without loss of efficacy. Overall, the following description establishes a new delivery strategy that is extremely useful for cell-based assays, cellular imaging applications, the ex vivo manipulation and reprogramming of cells, and other applications. This description is provided for the purpose of illustrating, not limiting, the subject matter disclosed herein.

Results

Figure 3:
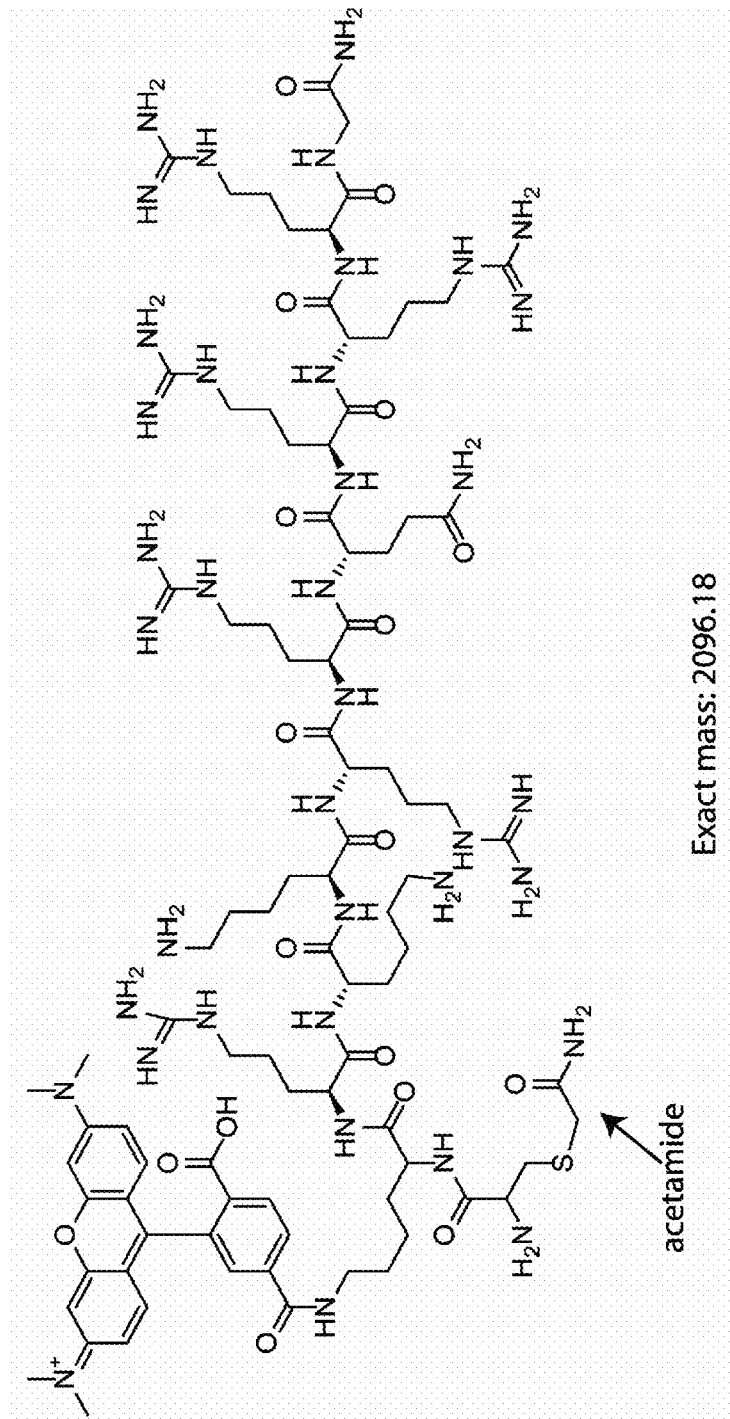
FIG. 3 illustrates the structure and expected mass of the acTAT construct.

A Disulfide-Bonded Dimer of TAT Penetrates the Cytosol of Cells More Efficiently than Monomeric Counterparts The CPP derived from a domain of the HIV transactivating transcriptional activator with the sequence XKKXXQXXX (see SEQ ID NO:1, wherein all residues designated with X are arginines (Arg: R); referred to herein as "TAT CPP domain") was used as a template for the design of a dimeric delivery vehicle. A C-terminal glycine (Gly; G) was added to the CPP domain for synthetic purposes to prevent racemization upon attachment to resin during solid phase peptide synthesis. However, the C-terminal glycine is not believed to have a role in the functionality of the TAT CPP domain, which is demonstrated below. Finally, a C-terminal amide (C(=O)—NH$_2$) was incorporated to avoid any additional charge provided by the typical carboxylic at the C-terminus when deprotonated. A lysine modified with the fluorophore tetramethylrhodamine (TMR) was introduced for fluorescence imaging and a cysteine was added at the N-terminus of TAT to permit dimerization by disulfide bond formation (FIG. 1). Disulfide bonds are relatively stable inside endosomes, but are cleaved upon entry into the reducing cytosol. Thus, a dimeric TAT construct (FIG. 2) might be stable and endosomolytic inside endosomes, but become monomeric and lose its membrane disruption activity upon entering the cytosol. The monomer product, CK(TMR)-TAT was purified as a reduced monomer. The term "TAT", as used herein, refers to the monomer product (i.e., CK(TMR)-TAT) and not the TAT CPP domain, unless otherwise indicated. Incubation in oxygenated media and oxidation of the free cysteine thiol of TAT generated the dimer $(CK(TMR)TAT)_2$ (referred to herein as "dimeric TAT" or "dTAT"), wherein each monomeric TAT unit is linked via a disulfide bond between the end cytosine residues. TAT and dTAT were characterized by HPLC and MALDITOF MS spectrum analysis. Purified CK($\epsilon$-NH-TMR)TAT (TAT) exhibited a retention time (rt) of 14.2 min (TAT, expected mass=2039.16, observed mass=2040.66). dTAT was obtained by incubating TAT in oxygenated buffer overnight. After HPLC purification, dTAT showed a single peak with a retention time (rt) of 22.7 min (dTAT, expected mass=4076.30, observed mass: $M+1/1H^+=4084.21$ Da, $M+2/2H^+=2041.32$). Pure dTAT was mixed with a solution of TCEP (50 mM) in water and allowed to react for 15 min. The HPLC chromatogram showed a peak with rt=14.3 min and was identical to the retention time of pure TAT (not shown). Alternatively, the thiol of TAT (i.e., CK(TMR)TAT) was acetamidated to obtain a peptide (referred to herein as "acTAT"), which cannot dimerize (FIG. 3). acTAT was characterized by HPLC and MALDI-TOF MS spectrum analysis of pure acTAT (rt=8.93 min) (expected mass: 2096.18, observed mass: 2096.31) (not shown).

Figure 4A:
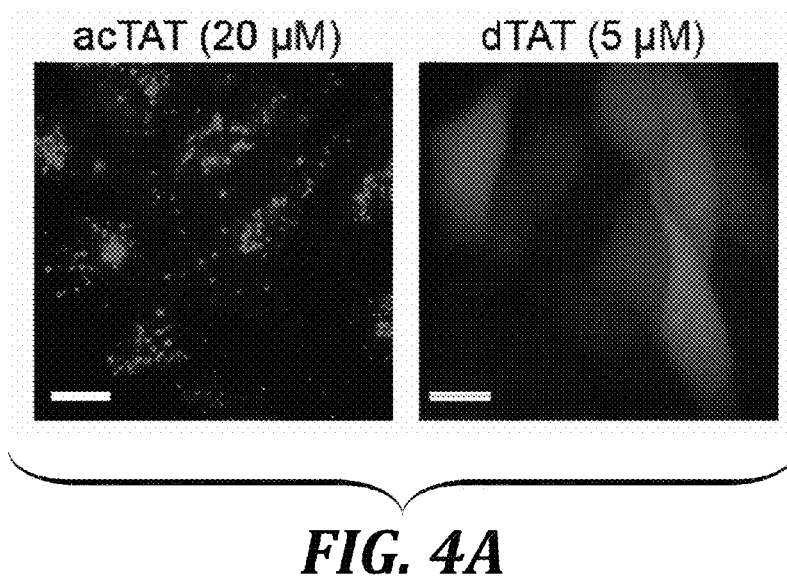
FIGS. 4A-4D illustrate the cytosolic delivery of dTAT in live cells is efficient and exceeds its monomeric counterparts.
Figure 4B:
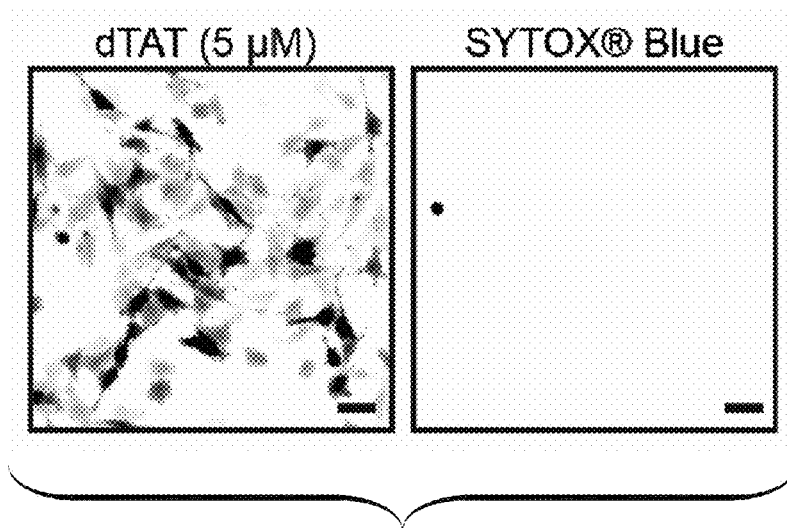
Figure 4C:
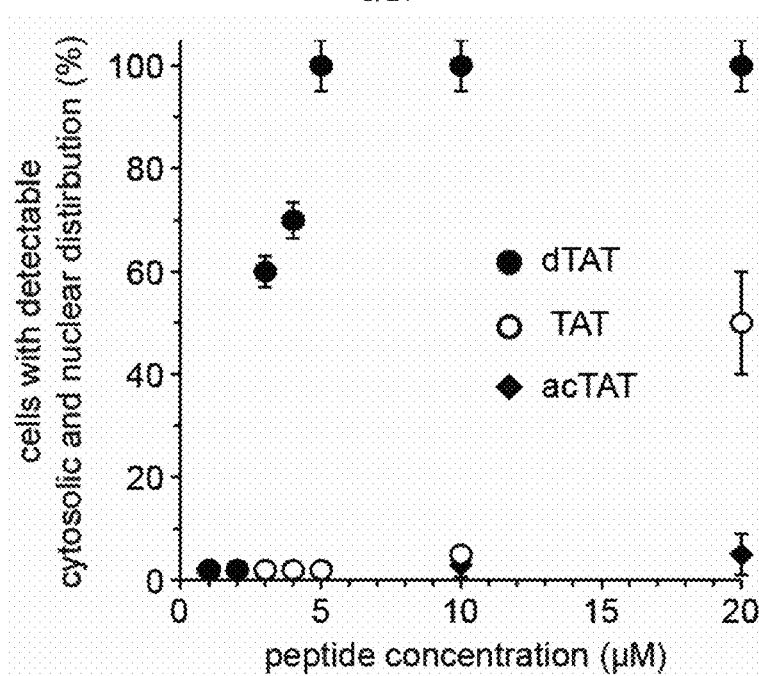
Figure 4D:
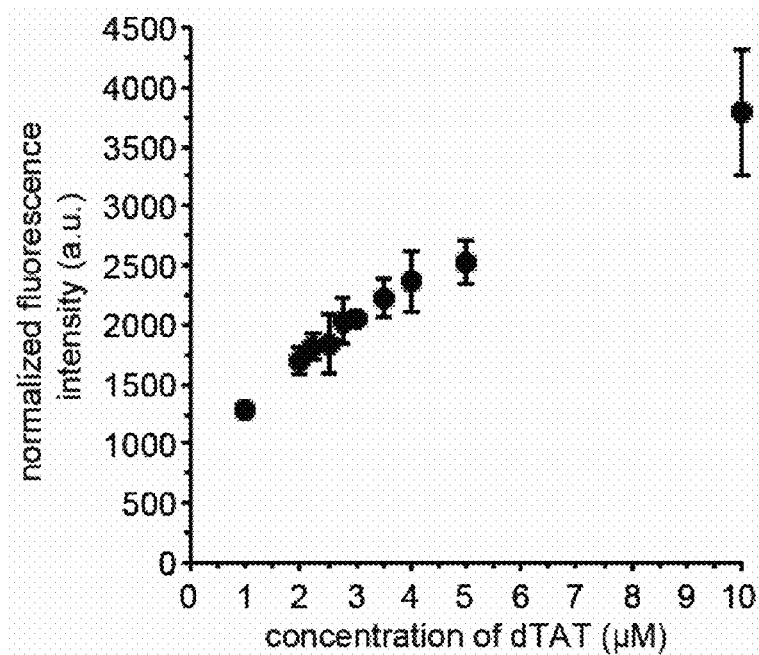
Figure 5:
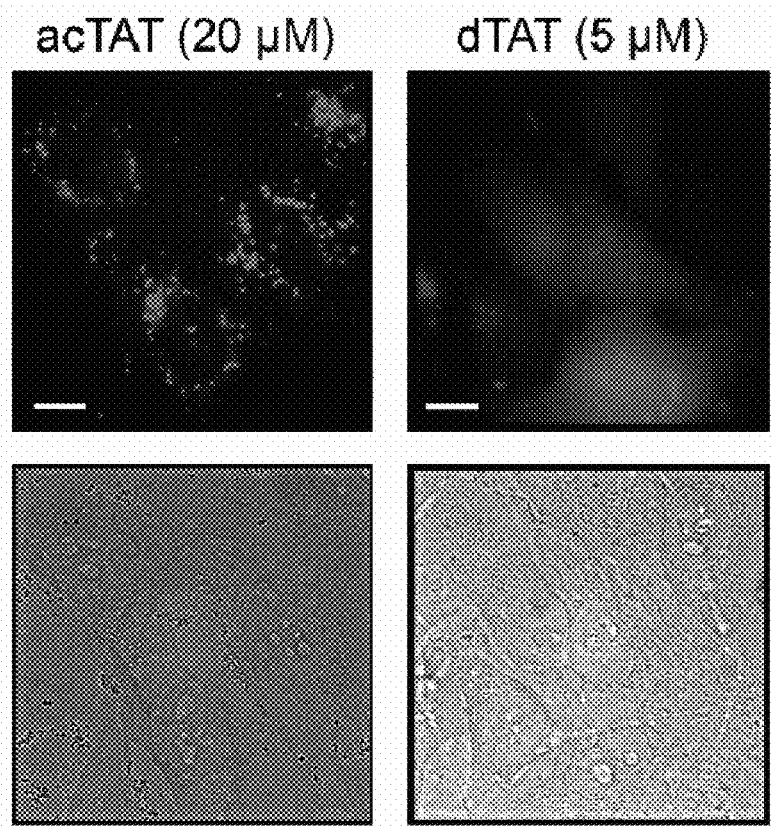
FIG. 5 illustrates that the cellular localization of acTAT and dTAT is different after incubation with live cells. Fluorescence (top panels) and bright field images (bottom panels) (using 100× objective) of HeLa cells incubated with 20 μM acTAT (left panels) and 5 μM dTAT (right panels). The acTAT peptide displays a fluorescence punctate distribution while dTAT exhibits a cytosolic and nuclear fluorescence distribution. Bright field images show no change in HeLa cell morphology upon peptide delivery. Scale bar, 10 μm.
Figure 6:
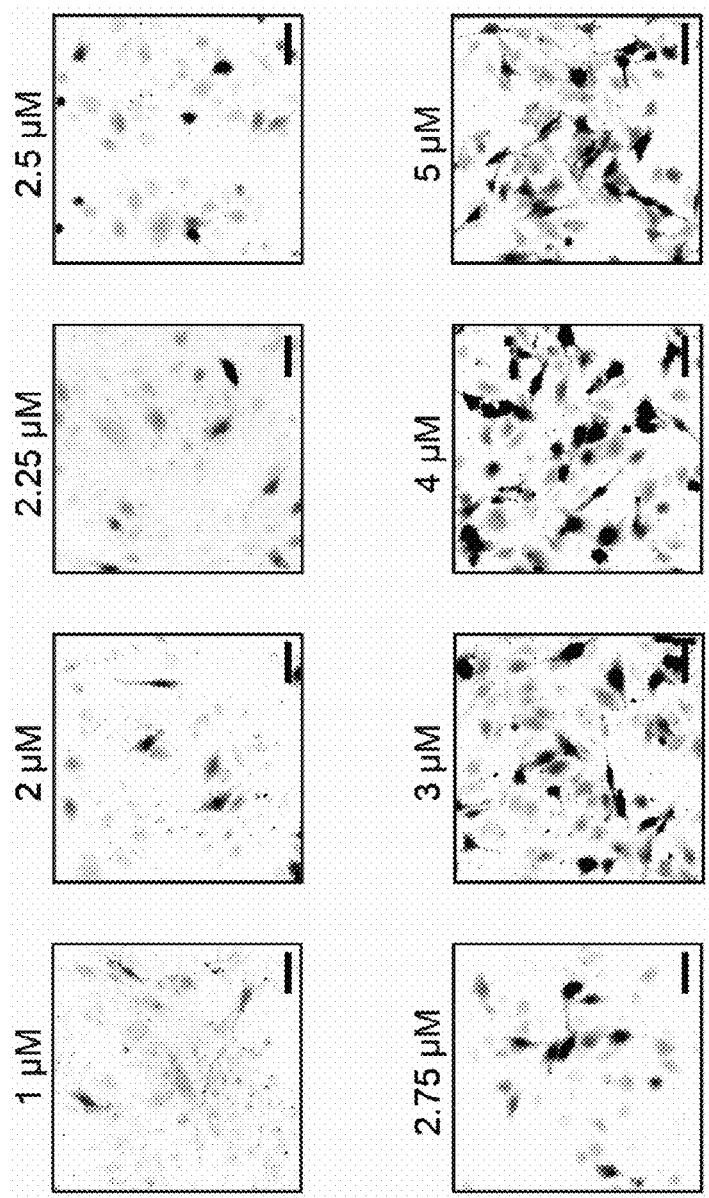
FIG. 6 illustrates that cytosolic and nuclear fluorescence distribution of dTAT is concentration dependent. HeLa cells were incubated with varying concentration of dTAT (1, 2, 2.5, 2.25, 2.5, 2.75, 3, 4, 5 μM). Cells were washed and imaged. Inverted monochrome images (20× objective) show a dramatic increase in the cytosolic delivery of the peptide between 2-5 μM. Although not shown here, the number of cells in each image is approximately the same as determined by bright field imaging. Cells that display a fluorescence punctate distribution are not clearly visible under these imaging conditions. Further analysis of these cells using a 100× objective clearly show a fluorescence punctate distribution indicative of peptides trapped in endosomes. Scale bars, 50 μm.
Figure 7A:
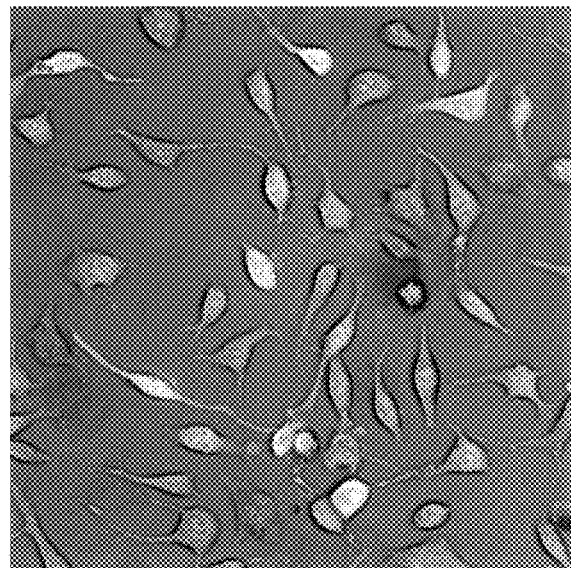
FIGS. 7A-7B illustrate the fluorescence images of dTAT delivery in dorsal root ganglion F11 (DRG-F11) neuronal cells. After 1 h of incubation with dTAT (5 μM), imaging was performed with 20× (FIG. 7A) and 100× (FIG. 7B) objectives.
Figure 7B:
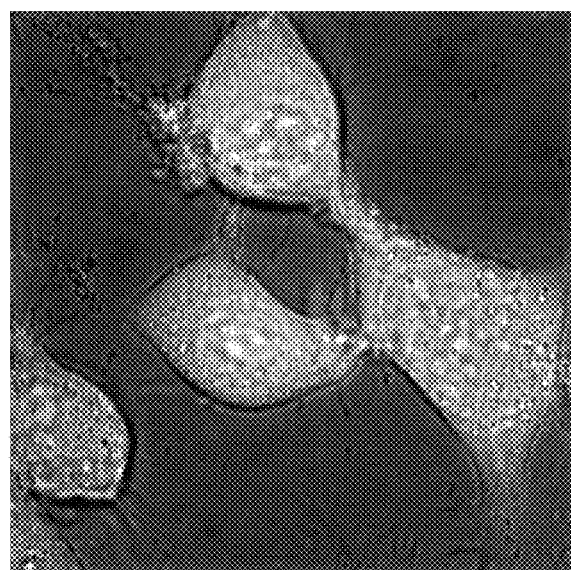

The TAT, dTAT and acTAT peptides were incubated for 1 h with several cell lines and internalization was assessed by fluorescence microscopy. FIGS. 4A-4D show acTAT (1-20 µM) localized in a punctate distribution consistent with accumulation of the peptide inside endosomes. In contrast, the fluorescence signal of dTAT was either punctate (below 2 µM) or distributed in the cytosol and nucleus (above 5 µM). See also FIG. 5. Interestingly, the number of cells with a diffuse fluorescence distribution increased dramatically between 2 and 5 µM of dTAT (FIG. 4C and FIG. 6). The overall amount of dTAT inside cells (cytosol+endosomes), measured by bulk fluorescence of lysates, was however almost linearly correlated to the concentration of dTAT administered extracellularly (FIG. 4D). These data demonstrate that dTAT is endocytosed and that it escapes into the cytosol of cells above a threshold concentration. Cytosolic delivery of dTAT was achieved in HeLa, NIH 3T3, HaCaT, and COLO 316 cells. Briefly, delivery of dTAT into the cytosol and nucleus of live cells was achieved in multiple cell lines. The cell lines HeLa, NIH 3T3, COLO 316 and HaCaT were incubated with 5 µM dTAT for 1 h, washed and imaged. The fluorescence signal detected was in the cytosol and nucleus of cells. After imaging, cells were incubated at 37° C. in a humidified atmosphere containing 5% $CO_2$ for 24 h, washed and imaged again. The cell morphology did not change after 24 h. Cell viability was assessed by exclusion of the cell-impermeable nuclear stain SYTOX® Blue at both 1 h and 24 h time point. The TMR fluorescence at the 24 h time point was different to that obtained at the 1 h time point presumably because of the intracellular degradation of the peptide (not shown). In all cases, cells were not stained with SYTOX® Blue, indicating that their plasma membrane was not compromised and that the cells were alive. Similar to acTAT, TAT was localized inside endosomes at up to 10 µM. However, at 20 µM, many cells display cytosolic fluorescence, indicating that TAT reproduces some of the activity of dTAT by possibly dimerizing in situ. Briefly, localization of TAT cellular after incubation with live cells appeared to depend on its concentration in the extracellular media. Inverted monochrome (black=fluorescence signal, white-no signal) fluorescence images were made of HeLa cells incubated with 10 or 20 µM of TAT for 1 h. TAT displayed at fluorescence punctuate distribution at 10 µM TAT while at 20 µM TAT showed a significant increase in the population of cells displaying cytosolic and nuclear fluorescence distribution (not shown).

dTAT Penetrates into the Cytosol of Cells Normally Resistant to Transfection

Dorsal root ganglion F11 (DRG-F11) neuronal cells are notoriously difficult to transfect. dTAT exposure was tested in DRG-F11 cells to determine whether the transfection difficulties also posed a barrier for dTAT. DRG-F11 cells were incubated for 1 hour with dTAT (5 µM). Imaging was performed with 20× (FIG. 18A) and 100× (FIG. 18A) objectives, which illustrate that dTAT penetrates into the cytosol of DRG-F11 cells.

dTAT Penetrates Cells by Endocytosis Followed by Endosomal Escape

Figure 8A:
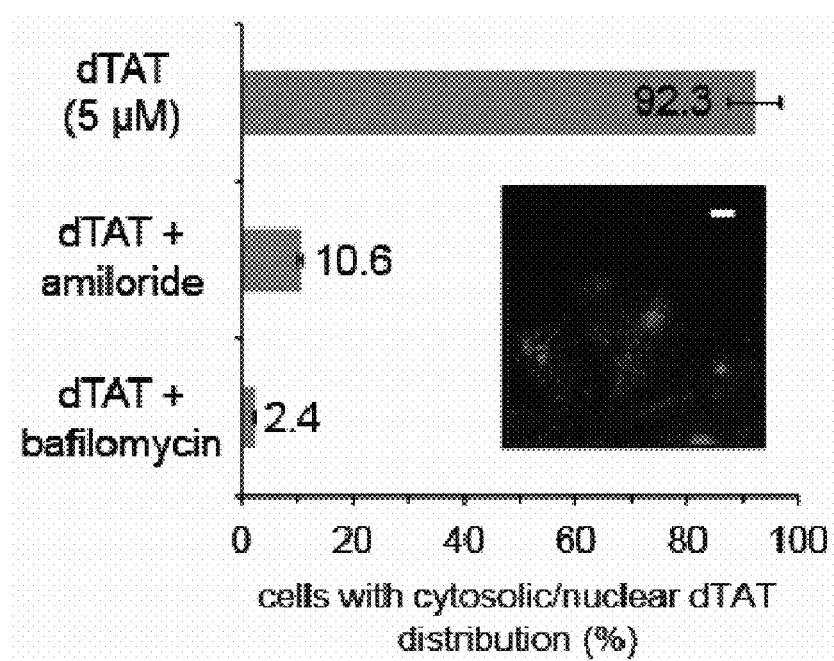
FIGS. 8A-8C illustrate that dTAT mediates endosomal escape.
Figure 8B:
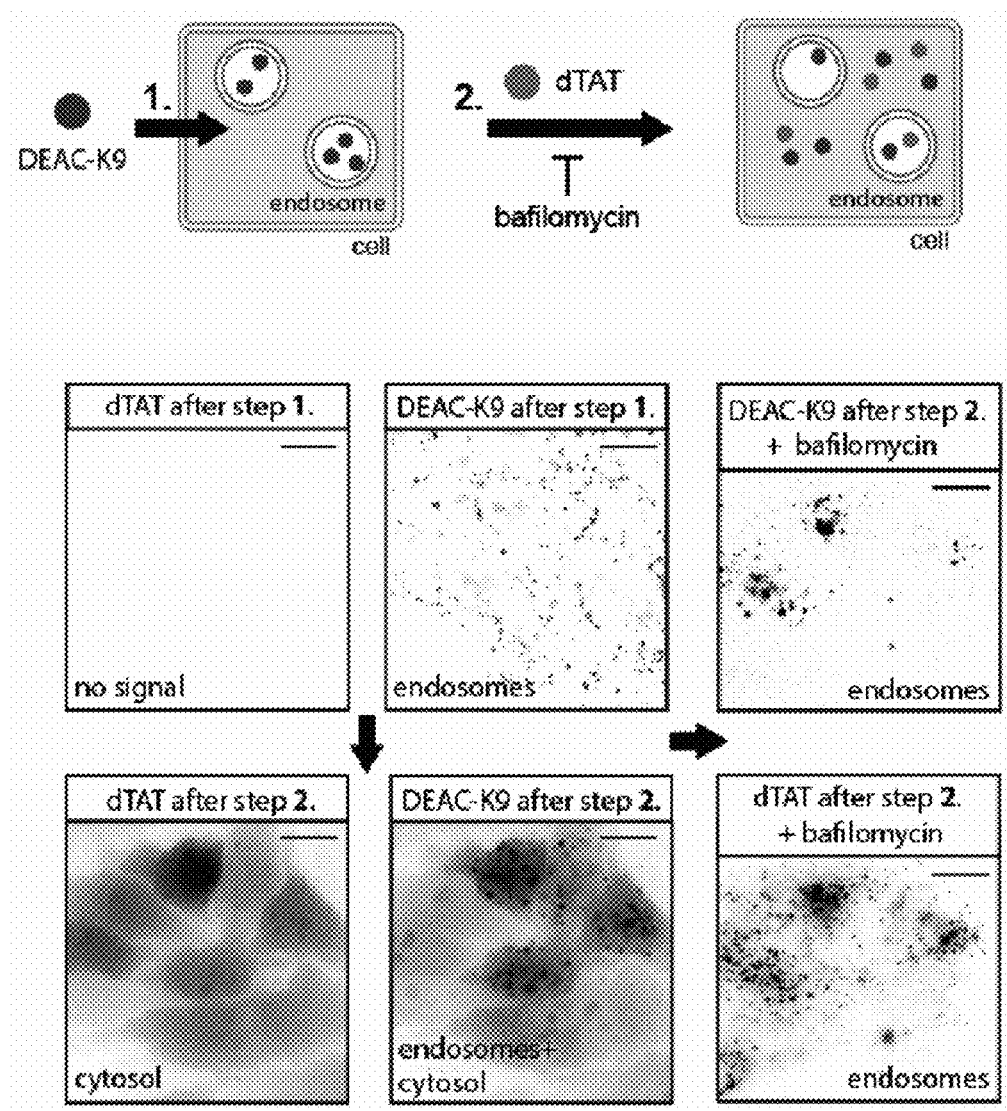
Figure 9:
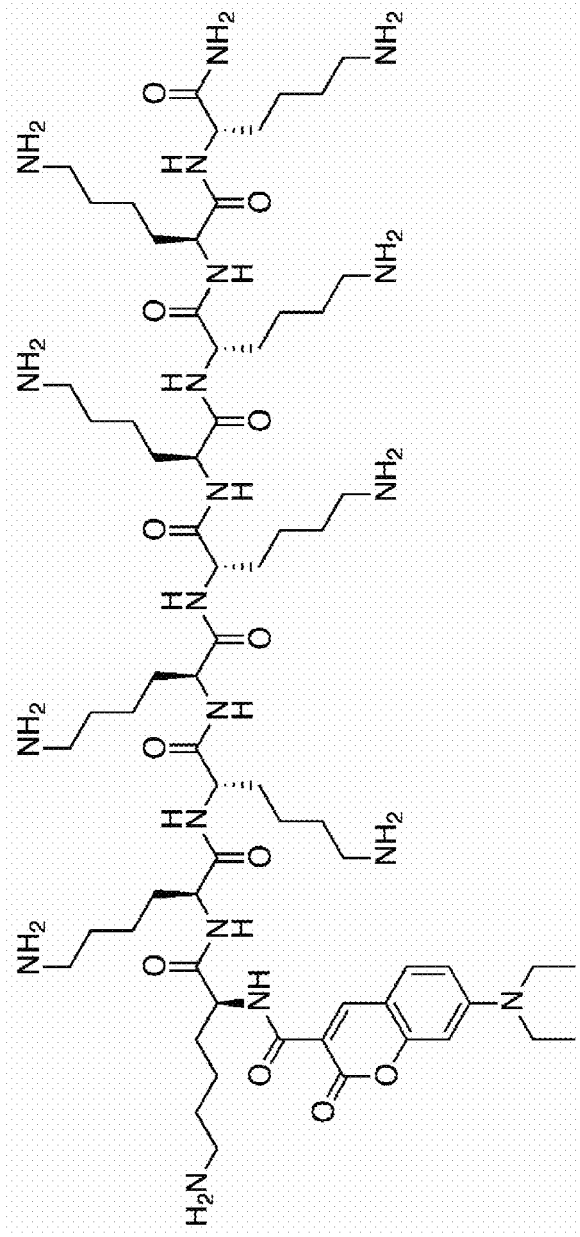
FIG. 9 illustrates the structure and expected mass of DEAC-K9.

To test whether endosomal escape is involved in delivery of dTAT, the effects of amiloride, a macropinocytosis inhibitor, and bafilomycin, an inhibitor of endosomal acidification, were assessed. FIG. 8A shows that amiloride and bafilomycin inhibited the cytosolic delivery of dTAT, suggesting that dTAT transits through the endocytic pathway before entering the cytosol of cells. To confirm these results, cells were incubated with DEAC-K9, a fluorescent polylysine peptide (see FIG. 9) that accumulates inside endosomes. Cells were then washed and incubated with dTAT (FIG. 8B). While only a punctate distribution of fluorescence was observed with cells incubated with DEAC-K9 alone, subsequent addition of dTAT led to redistribution of the DEAC signal throughout the cytosol and nucleus. This redistribution was however inhibited by bafilomycin. These data demonstrate that dTAT accumulates inside endosomes already containing DEAC-K9 and that dTAT escapes from endosomes in such a way that it is accompanied by release of DEAC-K9. Overall these data demonstrate that dTAT penetrates cells in a two-step process that includes endocytosis followed by escape from the endocytic pathway.

dTAT-Mediated Endosomal Leakage is Efficient

Figure 8C:
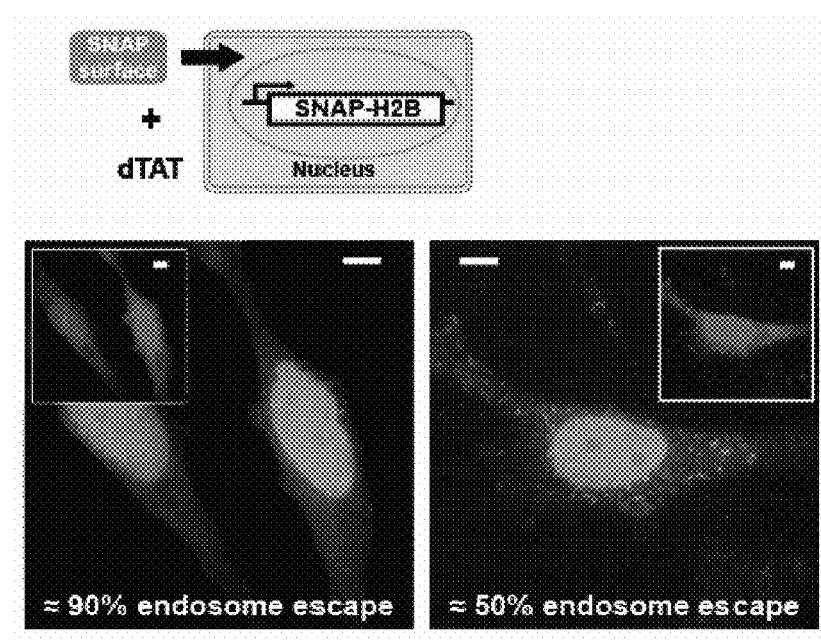

As demonstrated above, the cytosolic distribution of dTAT indicates an endosomal escape process significantly more efficient than what can be observed for acTAT or TAT. However, the cytosolic fluorescence of dTAT possibly obscures the signal that remains inside endosomes. Under such a hypothetical scenario, dTAT endosomal escape would appear more dramatic than it really is. To establish more precisely the efficiency with which dTAT mediates endosomal leakage, dTAT was coincubated with SNAP-Surface® 488, a cell-impermeable green fluorophore that can react with the SNAP protein fusion tag (see, e.g., Sun, X. et al. "Development of SNAP-Tag Fluorogenic Probes for Wash-Free Fluorescence Imaging," *Chembiochem: a European Journal of Chemical Biology* 12:2217-2226 (2017), incorporated herein by reference in its entirety. The experiment was performed in cells expressing SNAP-H2B histone construct so that SNAP-Surface® 488 would label the nucleus of cells upon delivery. Cells incubated with dTAT and SNAP Surface® 488 displayed a nuclear staining (FIG. 8C) while cells incubated with SNAP-Surface® 488 alone did not. Briefly, SNAP-Surface® 488 was shown to enter cells via endocytosis. HeLa cells were incubated with 5 µM SNAP-Surface® 488 for 1 h, washed and imaged. Inverted monochrome images showed a punctate fluorescence distribution from SNAP-Surface® 488. HeLa cells were incubated with 5 µM SNAP-Surface® 488 and 2.5 µM dTAT (a concentration in which dTAT incubation does not result in significant cytosolic release) for 1 h, washed and imaged. Inverted monochrome images again showed SNAP-Surface® 488 accumulation in endocytic organelles (punctate distribution) and colocalization with TMR signal. Bright field images showed HeLa cells morphology did not change after uptake of SNAP-Surface® 488 and/or dTAT (not shown). These data further confirm that the fluorescence detected is intracellular. Moreover, because SNAP-Surface® 488 accumulates in the nucleus after delivery, the cytosolic fluorescence is depleted and the amount of fluorescent molecules remaining inside endosomes is more clearly revealed. As highlighted in FIG. 8C, cells with a brightly labeled nucleus contained only few dim endosomes. It should be noted that SNAP-Surface® 488 fluorescence is quenched (80%) before it reacts with the SNAP fusion tag. When taking quenching into account, analysis of the fluorescence signal indicated that between 50% and 90% of the fluorescence escaped endosomes in the cells imaged (100 transfected cells were analyzed).

dTAT Mediated Cytosolic Delivery does not Affect Cell Viability, Cell Proliferation, or the Endocytic Route Used by dTAT Because dTAT-mediated endosomal escape is very efficient, a concern is that dTAT might hypothetically have a negative impact on cell physiology. To address this issue, the toxicity associated with dTAT was established 1, 24, and 48 h after incubation with HeLa cells. Surprisingly, the fraction of dead cells was below 5% at 5 µM dTAT, a concentration sufficient to achieve efficient cytosolic penetration in approximately all cells (FIG. 10B). The morphology of cells treated with dTAT was also identical to that of untreated cells (FIG. 10A) (the distribution of the TMR signal is different after 24 h, presumably because of peptide degradation). In addition, FIG. 10C shows that HeLa cells treated with dTAT (5 µM) grow at the same rate as untreated cells. Finally, cells containing a cytosolic fluorescence signal indicative of efficient dTAT endosomal escape were observed to divide by microscopy (FIG. 10D). Overall these data demonstrate that cells survive dTAT penetration and grow normally.

Figure 11:
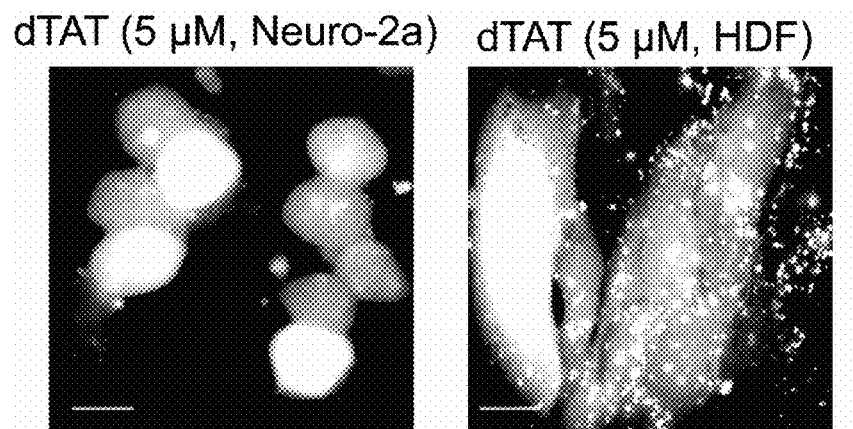
FIG. 11 illustrates the cellular localization of dTAT after 1 h incubation with neuronal cell line Neuro-2a (left panel) and primary human dermal fibroblasts (HDF) (right panel). Cells were incubated with dTAT, washed, and imaged with a 100× objective. Fluorescence images show cytosolic release for cells incubated with dTAT. Exclusion of SYTOX® blue (2 µM) was used to determined that the cells imaged do not have a compromised plasma membrane (not shown). Scale bars, 10 µm.
Figure 12:
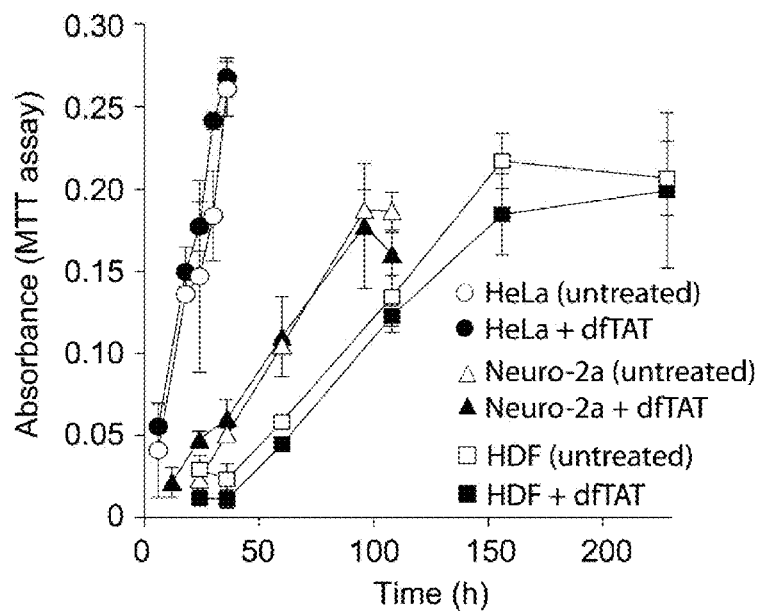
FIG. 12 illustrates that cells treated with dTAT proliferate at a rate identical to untreated cells. HeLa, Neuro-2a and HDF cells were incubated with 5 µM dTAT for 1 h or left untreated. Proliferation was assessed using a MTT assay for up to 36 h after incubation (150,000 cells/experiment, experiments in triplicates, average and standard deviations represented).

To determine whether this demonstrated lack of negative effect on cell morphology and proliferation is limited to HeLa cells, similar assays were performed for other cell types. FIG. 11 illustrates the cellular localization of dTAT after 1 h incubation with neuronal cell line Neuro-2a (left panel) and primary human dermal fibroblasts (HDF) (right panel). Cells were incubated with dTAT, washed, and imaged with a 100× objective. Fluorescence images show cytosolic release for cells incubated with dTAT. Exclusion of SYTOX® blue (2 µM) was used to determined that the cells imaged do not have a compromised plasma membrane. FIG. 12 graphically illustrates the proliferation rate (absorbance in an MTT assay) of treated and untreated HeLa, Neuro-2a, and HDF cells. The treated and untreated cells for each cell-type exhibited nearly identical proliferation patterns over time.

Figure 13:
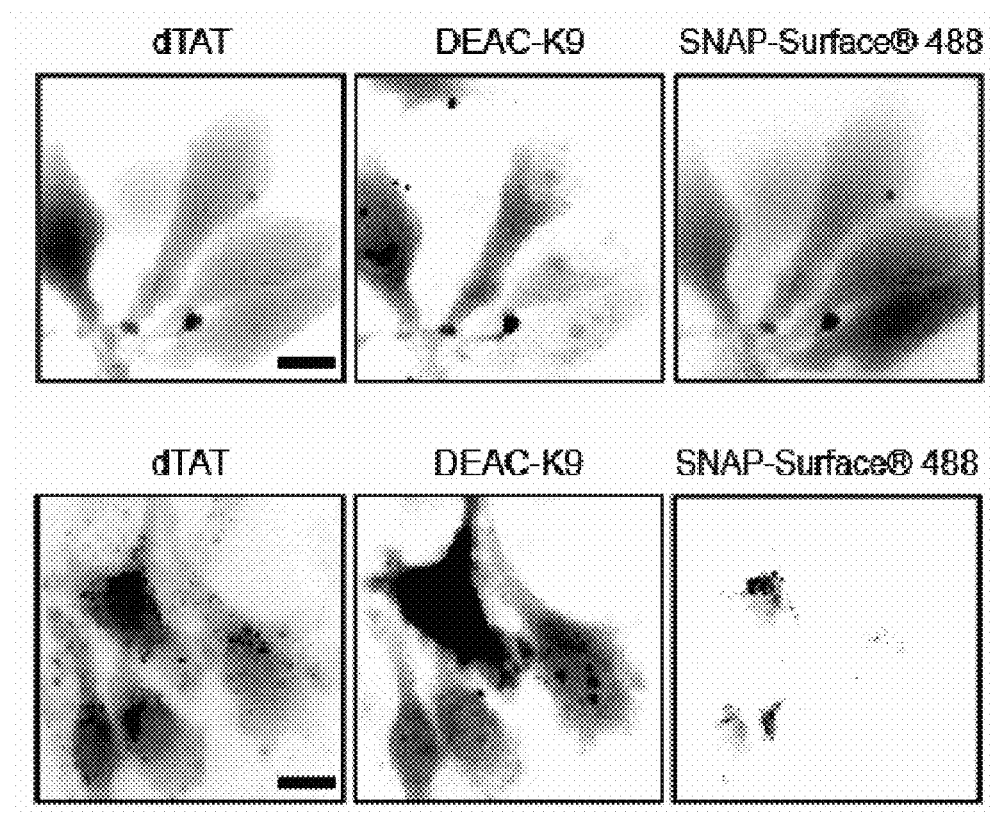
FIG. 13 illustrates that dTAT-mediated endosomal escape can be repeated. HeLa cells were co-incubated with dTAT (5 µM) and DEAC-K9 (5 µM) for 1 h (step 1) (both rows). After washing, dTAT (5 µM) and SNAP-Surface® 488 (5 µM) were co-incubated in the presence (bottom row) or absence of bafilomycin (200 nM) (top row) (step 3). Scale bars, 10 µm.

If dTAT perturbs many endosomes during a delivery step, endocytic trafficking might hypothetically be a likely cellular process that would be negatively affected following peptide incubation. For example, if dTAT disturbs the endocytic pathway dramatically it might hypothetically deliver a molecule successfully after an initial treatment but fail to deliver a second molecule with repeated dTAT incubation. To test this idea, the step-wise delivery of two different molecules (DEAC-K9 and SNAP-Surface® 488) was assessed. Cells were first incubated with dTAT (5 µM) and DEAC-K9 (5 µM) for 1 h. As expected, this incubation resulted in the cytosolic distribution of both dTAT and DEAC-K9 (data not shown). Twenty minutes later, cells were incubated with dTAT (5 µM) and SNAP-Surface® 488 (5 µM) for 1 h. Surprisingly, cells treated with this multiple-step protocol displayed cytosolic and nuclear fluorescence of both DEAC-K9 and SNAP-Surface® 488 (FIG. 13). Importantly, delivery of SNAP-Surface® 488 did not occur in the absence of dTAT during the multiple-step delivery protocol. Briefly, HeLa cells were first incubated with 5 µM dTAT and 5 µM DEAC-K9 for 1 h. Cells were then washed, incubated with 5 µM SNAP-Surface® 488 for 1 h and imaged. Inverted monochrome images showed cytosolic and nuclear localization of TMR and DEAC. However, SNAP-Surface® 488 displayed a fluorescence punctate distribution (not shown). Furthermore, delivery of SNAP-Surface® 488 was inhibited by bafilomycin, consistent with the notion that the second delivery step is also mediated by the endosomolytic activity of dTAT (FIG. 13). Moreover, the fluorescence of SNAP-Surface® 488 examined was comparable to that obtained if SNAP-Surface® 488 was delivered into untreated cells (one step delivery) or simultaneously with DEAC-K9 (FIGS. 14A-14B). Together these results establish that dTAT-mediated delivery can be repeated. This, in turn, establishes that the endocytic route employed by dTAT is not dramatically compromised after dTAT endosomal escape.

dTAT does not Elicit a Strong Transcriptional Response in Cells

Figure 15:
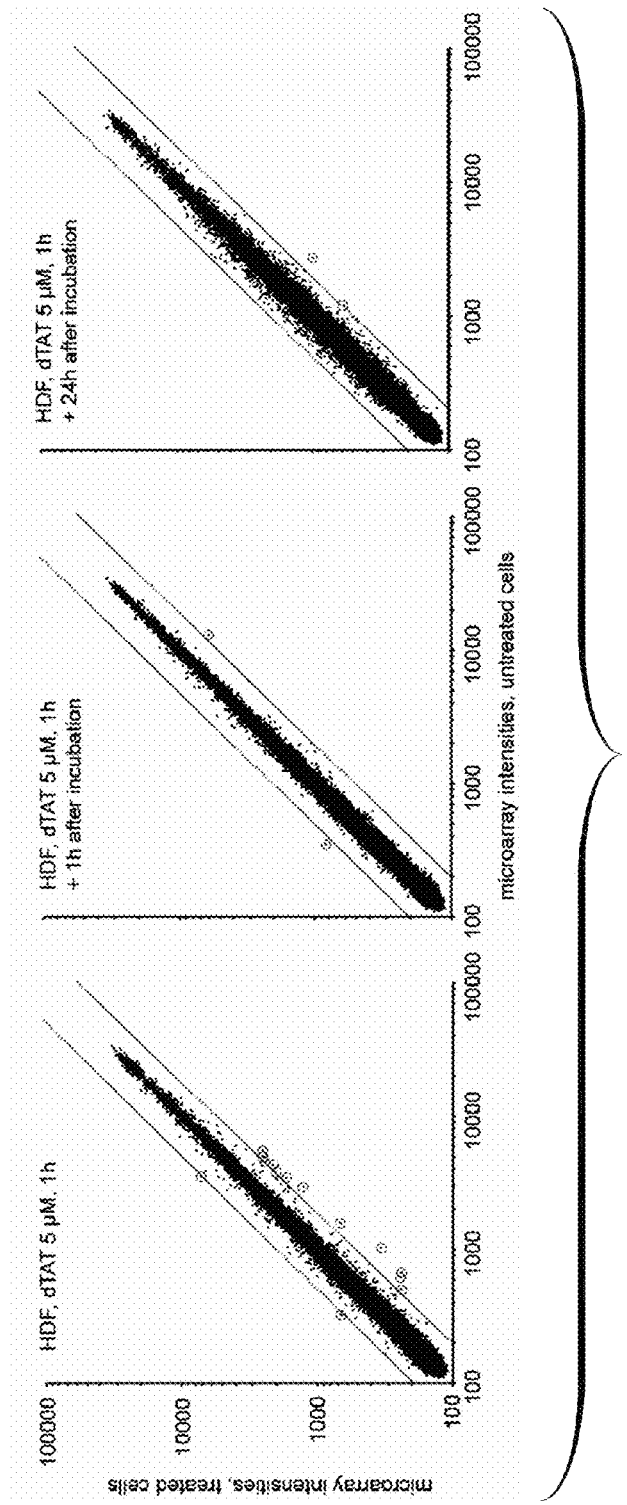
FIG. 15 illustrates that administration of dTAT does not elicit a strong transcriptional response in cells, and that cells rapidly recover from dTAT cytosolic penetration. Whole-genome microarray analysis was performed on cells treated with 5 µM dTAT for 1 h to determine whether transcriptional patterns are influenced. Analysis was performed immediately, 1 hr or 24 hrs after dTAT treatment. Plot displays microarray intensity values of treated vs. untreated (same incubation steps but without peptide) samples. The straight lines represent 2-fold intensity change cut-off.
Figure 16A:
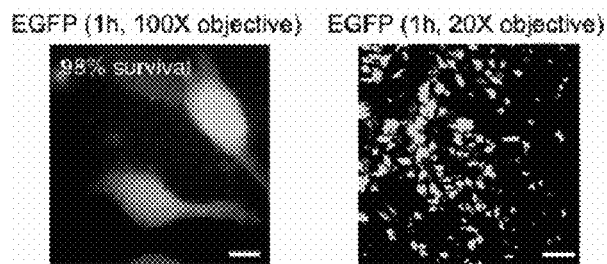
FIGS. 16A-16C illustrates the delivery of intact and functional proteins in trans using dTAT.
Figure 17:
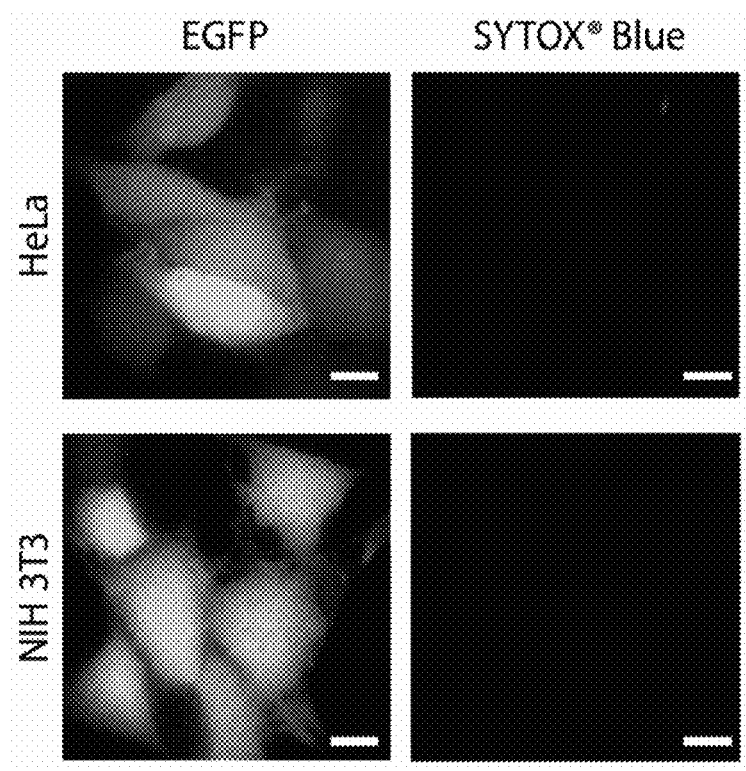
FIG. 17 illustrates the dTAT-mediated delivery of intact EGFP into different cell lines. HeLa (top panels) and NIH 3T3 (bottom panels) cells were incubated with EGFP (10 µM) and dTAT (5 µM) for 1 h, washed and imaged. Images show a homogenous cytosolic fluorescence distribution of EGFP in HeLa and NIH 3T3 cells. Scale bars, 10 µm.
Figure 18A:
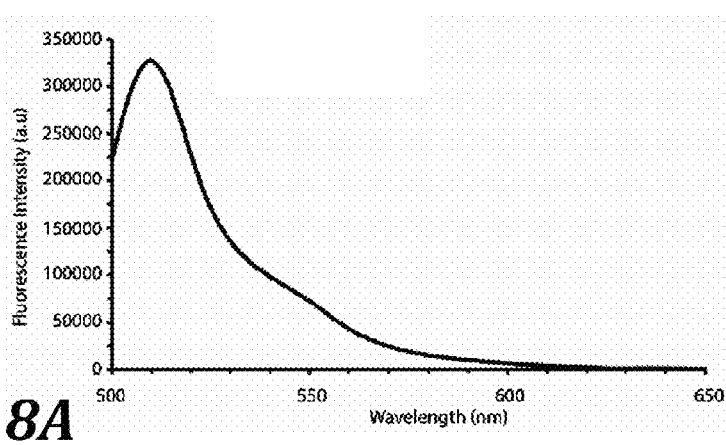
FIGS. 18A-18C illustrates that dTAT and EGFP do not interact when co-incubated.
Figure 18B:
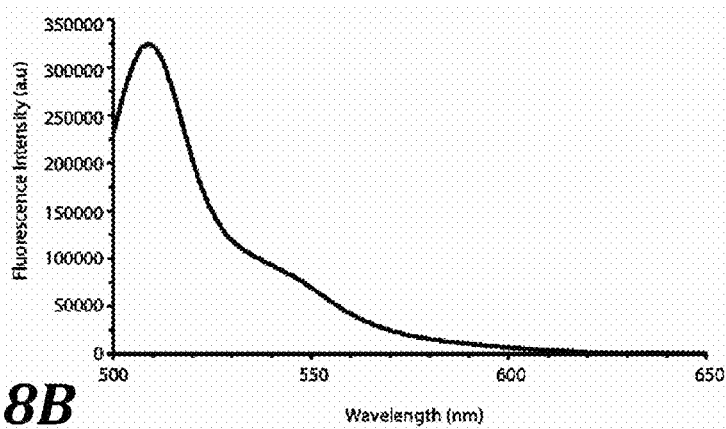
Figure 18C:
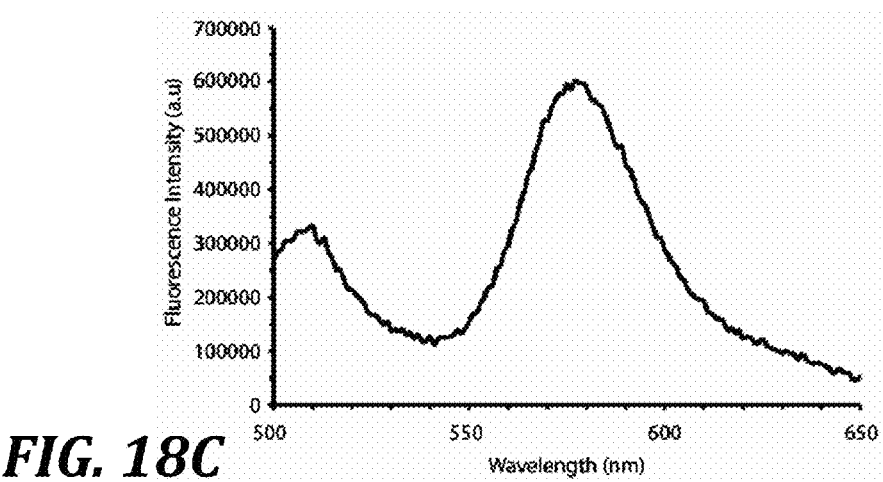

To better determine the effect of dTAT exposure on a cell, a whole-genome microarray analysis was performed on cells treated with 5 µM dTAT for 1 h to determine whether transcriptional patterns are influenced. Analysis was performed immediately, 1 h, or 24 h after dTAT treatment. FIG. 15 illustrates the plot displays microarray intensity values of treated vs. untreated (same incubation steps but without peptide) samples. The straight lines represent 2-fold intensity change cut-offs. These data illustrate that exposure to dTAT causes minimal transcriptional perturbations on a whole-genome scale.

dTAT Delivers Proteins into the Cytosol and Nucleus of Live Cells in Trans dTAT, DEAC-K9 and, SNAP-Surface® 488 are relatively small molecules. It was therefore addressed whether dTAT-mediated endosomal leakage could deliver large proteins into the cytosol of cells. For this assay, EGFP (26 kDa) was chosen as a model, since this protein is fluorescent only when properly folded. EGFP and dTAT were incubated for 1 h with cells and the protein distribution was examined by fluorescence. As observed with other cell-impermeable molecules, EGFP was distributed into the cytosol and nucleus in more than 90% of cells without observable toxicity (in HeLa or NIH 3T3 cells; see FIG. 16A and FIG. 17). While protein degradation might take place during delivery, this assay establishes that a population of folded protein is delivered. Moreover, a Förster resonance energy transfer (FRET) assay established that dTAT does not bind to EGFP (FIGS. 18A-18C). These results suggest that interactions between dTAT and a protein are not required for delivery.

Figure 16B:
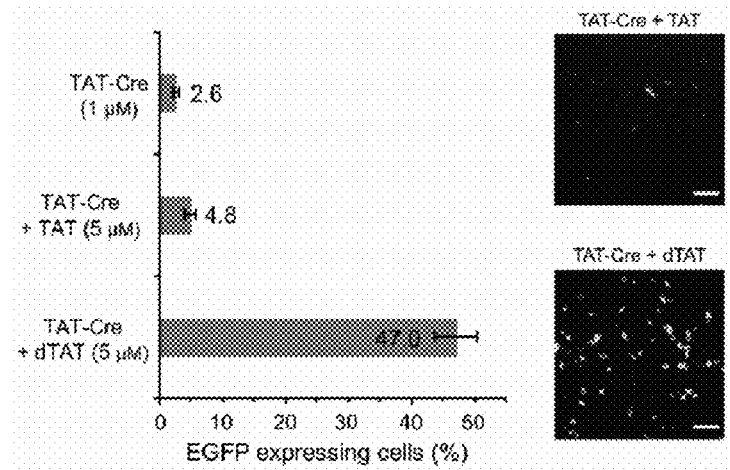
Figure 16C:
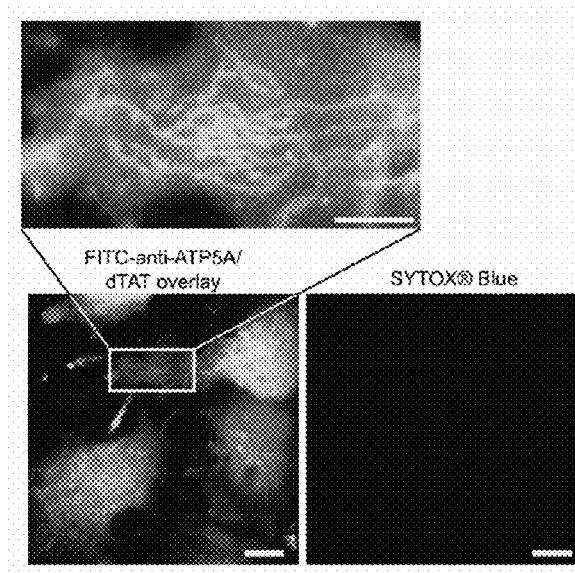
Figure 19A:
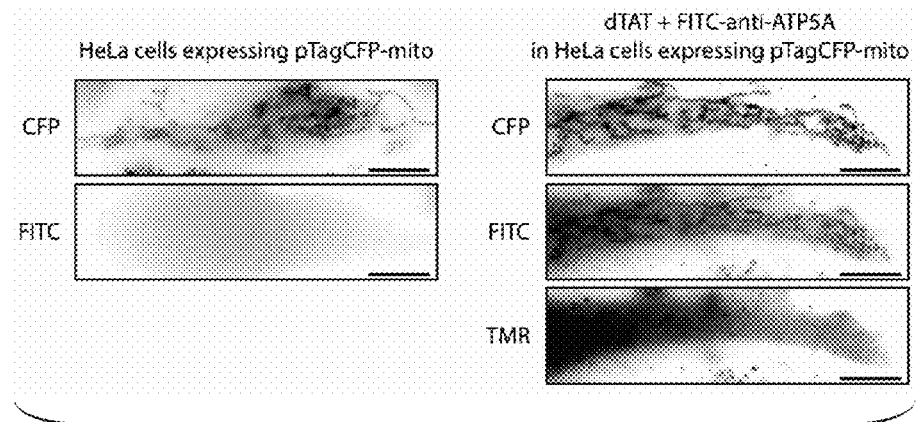
FIGS. 19A-19B illustrate that the FITC-anti-ATP5a antibody co-localizes with a fluorescently labeled mitochondrial protein expressed in live cells after dTAT-mediated delivery.
Figure 19B:
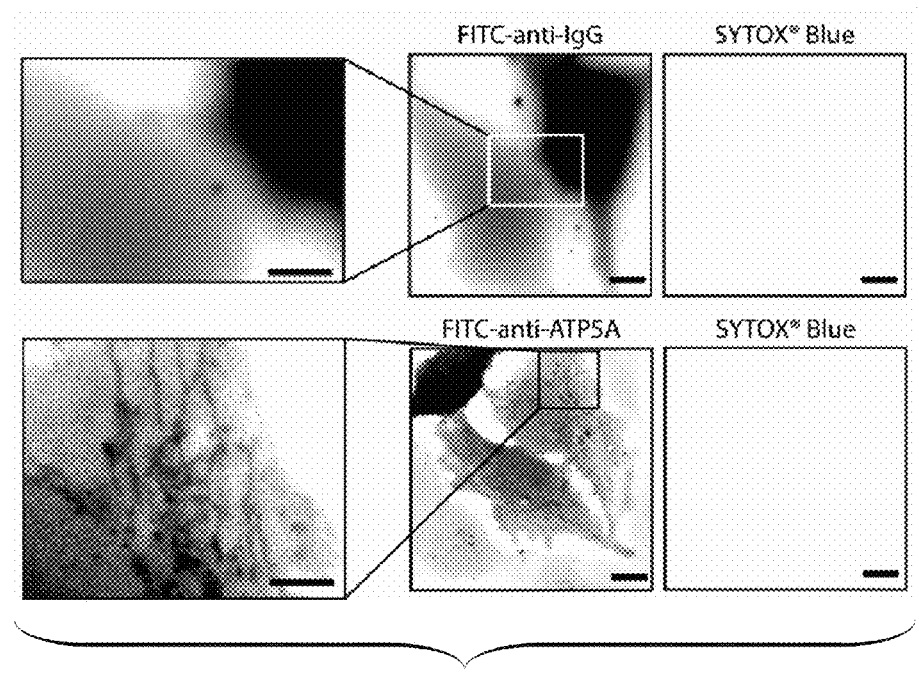

To further confirm that functional proteins can penetrate cells upon incubation with dTAT, delivery of Cre recombinase was tested. In this assay, Cre induces recombination of a loxP-STOP-loxP sequence upstream of the egfp gene of a reporter plasmid. Therefore, cells transfected with the reporter plasmid express EGFP when Cre recombinase penetrates cells and excises the STOP signal sequence (see, e.g., Wadia, J. S., et al., "Transducible TAT-HA fusogenic peptide enhances escape of TAT-fusion proteins after lipid raft macropinocytosis," *Nat Med* 10:310-315 (2004), incorporated herein by reference in its entirety). As shown in FIG. 16B, cells treated with TAT-Cre (1 µM) and dTAT (5 µM) expressed EGFP. Moreover, the percentage of EGFP+ cells was greater in the presence of dTAT (47%) than in the presence of TAT or when TAT-Cre was incubated alone (<5%). Next, the delivery of FITC-anti-ATP5A, a fluorescently labeled antibody that recognizes the alpha subunit of the mitochondrial ATP synthase, was examined. As shown in FIG. 16C, live cells treated with FITC-anti-ATP5A (20 µg/mL) and dTAT (5 µM) contained green-fluorescent tubular structures. Co-localization with the blue-fluorescent mitochondrial marker pTagCFP-mito confirmed that these structures are mitochondria (FIG. 19A). Finally, cells treated with FITC-anti-IgG, an antibody that does not target mitochondria, did not present the same tubular structures (FIG. 19B). Together, these experiments confirm that dTAT can deliver a functional antibody into live cells.

Figure 20A:
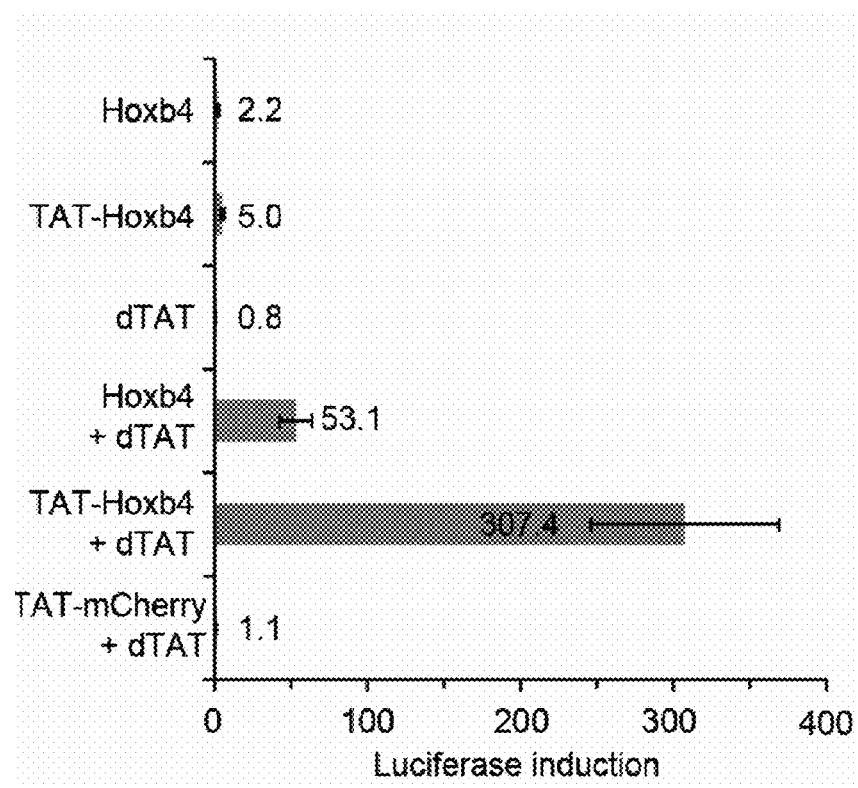
FIGS. 20A-20C illustrate that dTAT-mediated delivery improves and allows control of HoxB4 transcriptional activity.
Figure 20B:
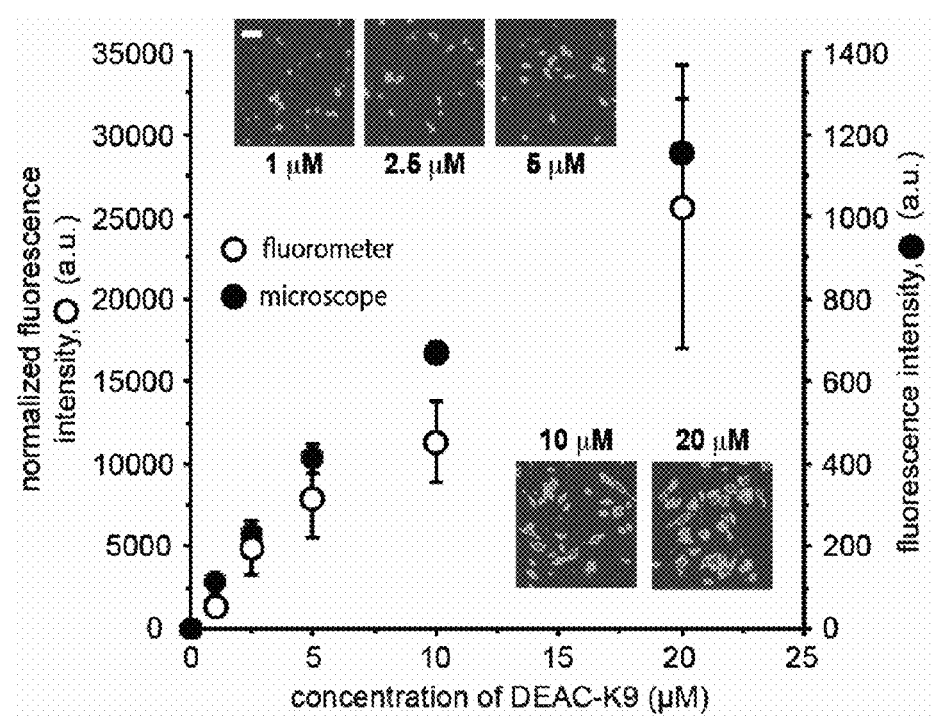
Figure 20C:
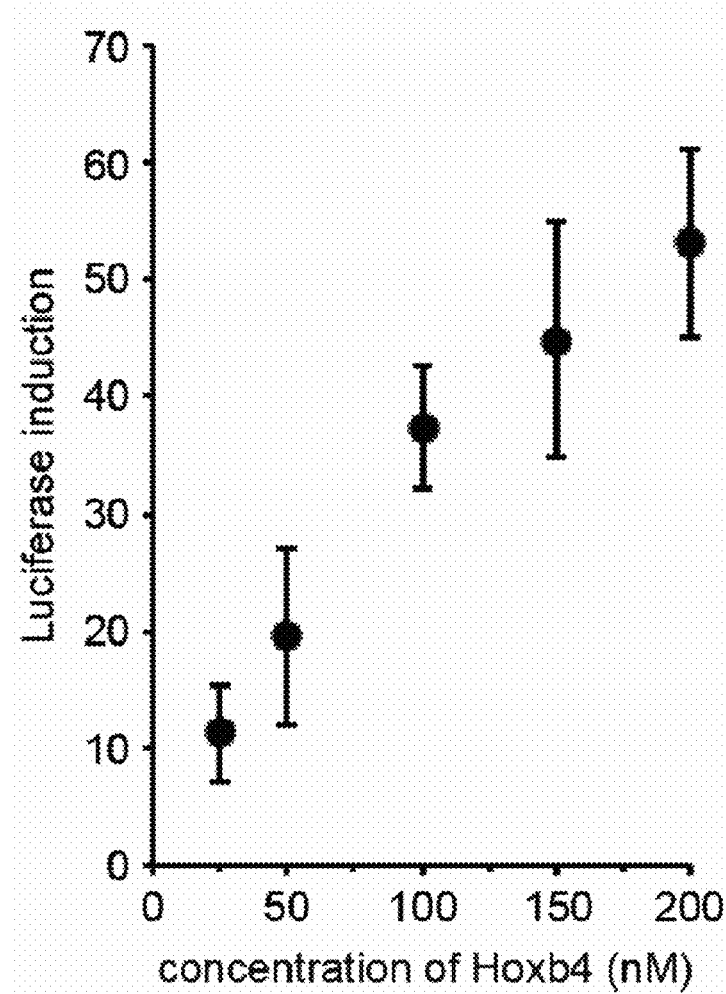

Next, the delivery of the therapeutically important transcription factor HoxB4 was tested. HoxB4 can penetrate cells by itself or when fused to the PDT TAT and activate transcription. Therefore, it was determined whether dTAT, by promoting cytosolic delivery, would enhance the transcriptional activity of the protein. NIH 3T3 cells were transfected with a vector containing the luciferase gene under a HoxB4-inducible promoter and with a β-galactosidase reporter as internal control. Cells were incubated with HoxB4 or TAT-HoxB4, in the absence or presence of dTAT for 1.5 h. Cells were then lysed and luciferase expression was assessed by measuring the luminescence of cell lysates normalized to β-galactosidase activity. FIG. 20A shows that HoxB4 and TAT-HoxB4 (200 nM) alone induced a 2.2 and 5.0-fold increase, respectively, in luciferase activity over the activity obtained from cells that were not treated with these proteins. These values are consistent with previously published reports. In contrast, addition of dTAT (3 µM), led to a luciferase induction of 53.1 and 307.4, respectively. The luciferase induction was therefore increased 24-fold in the presence of dTAT for HoxB4 and 61-fold for TAT-HoxB4. Neither dTAT alone nor dTAT incubated with TAT-mCherry led to the induction of luciferase, indicating that luciferase expression is dependent on the presence of HoxB4. While increasing the transcriptional output of HoxB4 is valuable, high levels of HoxB4 expression can result in anti-proliferative and transforming effects. Precisely controlling the level and activity of HoxB4 inside cells is therefore important to achieve a desirable biological outcome. Because dTAT appears to act independently of the molecules used for co-incubation in our assays, it was hypothesized that it might be possible to titrate the amount of protein that penetrates cells by varying the protein concentration in the media while keeping dTAT concentration constant. Under this scenario, the efficiency of endosomal escape should remain unaffected but the amount of material released from endosomes should change. Initial experiments with DEAC-K9 showed that the amount of fluorescent peptide delivered inside cells could be titrated using this protocol (FIG. 20B). Consistent with these results, luciferase induction responded linearly with the concentration of HoxB4 in the media (FIG. 20C). Together these results show that improved delivery leads to increased biological activity of proteins administered extracellularly and that the activity of delivered molecules can be precisely modulated.

Figure 22A:
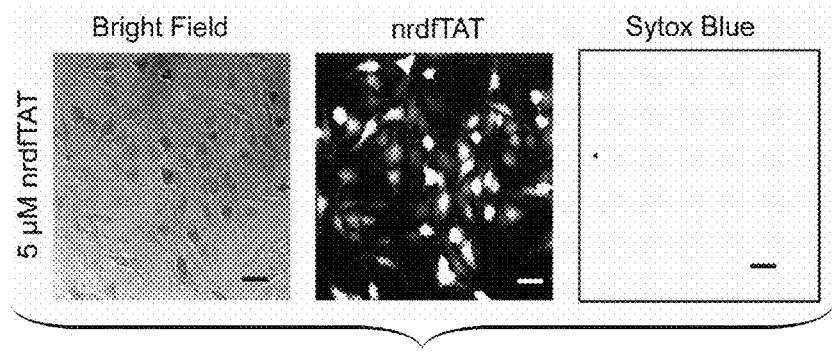
FIGS. 22A-22B illustrate the cytosolic delivery of nrdTAT into live cells. HeLa cells were incubated with 2.5-5 μM nrdTAT (FIG. 22A) and 5-10 μM nrdfTAT (FIG. 22B) for 1 h. Bright field images (left panels), monochrome fluorescence images (center panels; white-fluorescence signal, black=no signal); and cell viability with SYTOX Blue (2 μM) used as an indicator of cell death (right panels). The data show cytosolic delivery of nrdfTAT into HeLa cells at both concentrations. Scale bars, 50 μm (Inverted monochrome 20× image).
Figure 22B:
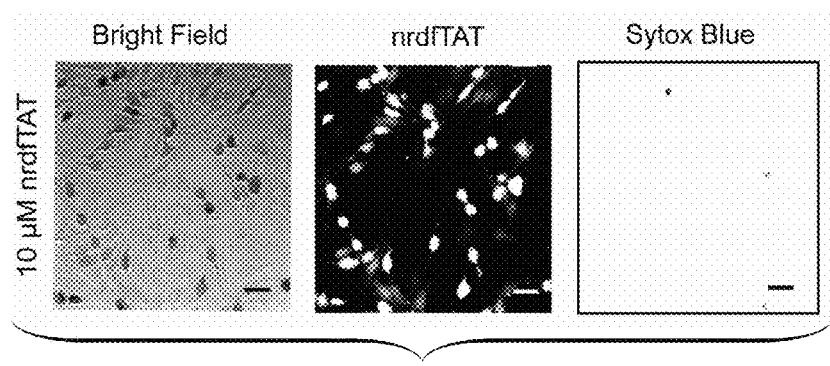

The Structural Linkage Between Each TAT Monomer in dTAT can be Changed without Affecting Cell-Penetration Activity In order to determine the relevance of the disulfide linkage that holds dTAT in its dimeric form, an alternative dimeric TAT construct was constructed. Specifically, a dimeric TAT construct where the disulfide bond linker is substituted with a non-reducible linker (nrdTAT) was constructed. The structure and expected mass of this particular nrdTAT construct is illustrated in FIG. 21. The structural linkage between each TAT monomer in dTAT can be changed without affecting cell-penetration activity. The rdTAT construct was tested for the general cell penetration activity, as described in more detail above. HeLa cells were incubated with 5 µM and 10 µM nrdTAT for 1 h. FIGS. 22A and 22B illustrate the respective bright field images (left panels), monochrome fluorescence images (center panels; white=fluorescence signal, black=no signal); and cell viability with SYTOX Blue (2 µM) used as an indicator of cell death (right panels). These data show efficient cytosolic delivery of nrdTAT into HeLa cells at both concentrations without negatively affective the cell biology. Accordingly, the linker linking the TAT peptides in a dimer construct does not need to be a disulfide linker, but rather can be changed to incorporate different functionalities while retaining the cell penetration activity described above.

Figure 23:
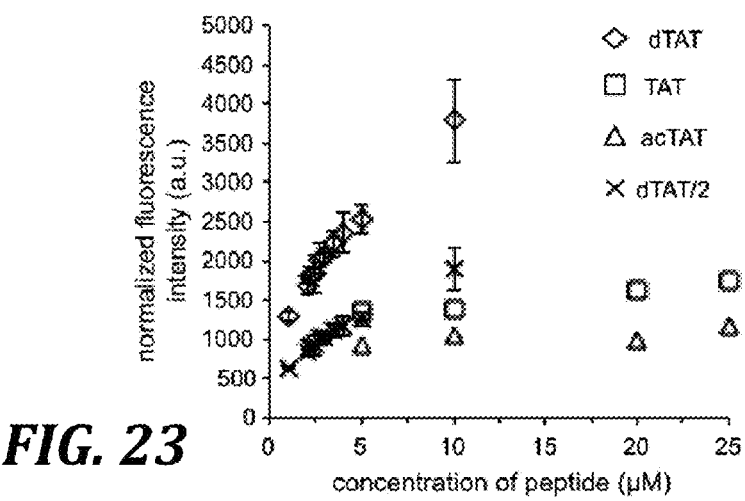
FIG. 23 illustrates the peptide uptake in HeLa cells as a function of the concentration of peptide present in the media. The uptake of the three peptides by HeLa cells was measured as a function of concentration (μM). Cells were incubated with either acTAT (5-25 μM), TAT (5-25 μM) or dTAT (1-10 μM) and the bulk fluorescence of cell lysates on a 96-well plate was measured using a plate reader. The fluorescence of each sample was normalized to total protein content in the cell lysate, as determined by a Bradford protein assay. Data shows a linear increase in the fluorescence uptake of cells incubated with dTAT. The lysis buffer used in this experiment contains 2 mM DTT. dTAT is reduced to the monomeric TAT upon this treatment. Consequently, the normalized fluorescence of dTAT was divided by two (dTAT/2) to compare the uptake of dTAT to that of TAT (the signal of one molecule of dTAT gives a signal twice that of a molecule of internalized TAT in this assay).

Discussion dTAT is remarkably efficient at delivering proteins, peptides, or small molecules into the cytosol or nucleus of live cells. In particular, dTAT mediates the release of molecules trapped inside endosomes. Delivery is efficient because the amount of material that reaches the cytosol is substantial, the amount of material that remains trapped inside endosomes is relatively low, and because cytosolic delivery occurs in most cells present in a sample. Endosomal escape appears to take place in most cells once dTAT reaches a threshold concentration within endosomes. Importantly, acTAT does not achieve endosomal escape even when the amount of monomeric peptide internalized is above this threshold level (FIG. 23). These results therefore suggest that dTAT is intrinsically more endosomolytic than its monomeric counterpart.

A remarkable aspect of dTAT-mediated delivery is the surprisingly low toxicity associated with the efficient endosomal escape observed. In contrast, light-induced endosomal lysis has been shown to be extremely toxic by causing the rapid release of calcium into the cytosol of cells. Similar effects could therefore be expected from the endosomolytic activity of dTAT. In addition, the membrane damage expected to accompany endosomal leakage as well as the release of endosomal and lysosomal proteases could contribute to toxicity. Yet, at 5 µM, a concentration at which cytosolic delivery is observed in more than 95% of cells, dTAT remarkably does not affect cell viability. Moreover, dTAT-mediated delivery does not have a negative impact on proliferation, indicating that cells are not only viable but also relatively healthy. Furthermore, these effects are observed for a variety of distinct cell-types, including cells notoriously resistant to standard transfection techniques.

dTAT delivers cell-impermeable molecules displaying diverse structures and properties. DEAC-K9, like dTAT, is highly positively charged and the pI of Cre (9.4), and HoxB4 (9.8) are also not suggestive of favorable electrostatic interactions with dTAT. EGFP, a protein with a lower pI (6.2), does not significantly interact with dTAT in vitro. It is therefore likely that dTAT does not interact significantly with the molecules tested outside the cell or within the lumen of endosomes.

The co-incubation format used herein allows several cargos to be incubated and delivered at once. Alternatively, delivery can be performed in successive steps. dTAT-mediated delivery does not require complex sample preparations and, as exemplified by the delivery of SNAP-surface 488 or FITC-anti-ATP5A, it is ideally suited for imaging applications. In addition, co-incubation also provides the opportunity to vary the concentration of target molecules independently to that of dTAT. In these assays, the concentration of dTAT was, for instance, kept constant (i.e., 5 µM) in order to maintain a high efficiency of endosomal release in most cells. By varying the concentration of DEAC-K9 or HoxB4 in the media, the amount of material delivered to the cytosol and the biological output, respectively, could in turn be titrated. While this approach is presumably not optimal for in vivo delivery of biologics, it offers several advantages in the context of tissue cultures and ex vivo manipulation of cells. Continuous overexpression of HoxB4 after retroviral delivery, in addition to promoting hematopoietic stem cell expansion, can also lead to malignant transformation, reduce proliferation or sensitize cells to apoptosis. These different outcomes are HoxB4 dose-dependent. dTAT-mediated delivery, by permitting HoxB4 levels and activity to be precisely controlled, could provide a solution to this problem. This, along with the lack of genetic manipulation associated with DNA-based approach, could contribute to making cell-therapy approaches safer for patients.

EXAMPLES

Materials and Methods

Peptides Design, Synthesis, and Purification

All peptides were synthesized in-house on the rink amide MBHA resin (Novabiochem, San Diego, Calif.) by SPPS using standard Fmoc protocols. Fmoc-Lys(Mtt)-OH, Fmoc-Lys(Boc)-OH, Fmoc-Gly-OH, Fmoc-Arg(Pbf)-OH, Fmoc-Gln(Trt)-OH, and Fmoc-Cys(Trt)-OH (Novabiochem) were used to assemble the peptides. Reactions were carried out in a SPPS vessel at room temperature using a stream of dry $N_2$ to provide agitation. Fmoc deprotection was performed by addition of piperidine in dimethylformamide (DMF) (Fisher, Waltham, Mass.) (20%, 10 mL) to the Fmoc-peptide resin (0.30 mmol). Deprotection reactions were carried out for 1×5 min and 1×15 min with a washing step in between reactions. Amino acid coupling reactions were carried out for 4 h with a mixture of Fmoc-amino acid (1.2 mmol), HBTU (Novabiochem) (0.44 g, 1.1 mmol), and diisopropylethylamine (DIEA) (Sigma, St. Louis, Mo.) (0.51 mL, 3.0 mmol) in DMF. Upon completion of the reactions, the resin was washed with DMF and dichloromethane (DCM) (Fisher, Waltham, Mass.). For DEAC-K9, the DEAC fluorophore (AnaSpec, Fremont, Calif.) was coupled to the N-terminus of the peptide after coupling of the ninth Fmoc-Lys(Boc)-OH using a mixture of DEAC, HBTU, and DIEA (4, 3.9, and 10 equiv in respect to the peptide) in DMF. The reaction was carried out overnight using a stream of dry $N_2$ to provide agitation. For CK(ε-NH-TMR)TAT (TAT), the Mtt protecting group at the ε-amino group of Lys on CK(ε-NH-Mtt)TAT was cleaved with 2% trifluoroacetic acid (TFA) (Fisher) and 2% triisopropylsilane (TIS) (Sigma) in DCM, and the resin was washed with DCM and DMF. A mixture of TMR, HBTU, and DIEA (4, 3.9, and 10 equiv in respect to the peptide) in DMF was added to the resin and the reaction was carried out overnight using dry $N_2$ to provide agitation. Following Fmoc-deprotection and peptide assembly, the resin was washed with DCM and dried in vacuo. The resin was then treated with TFA containing 2.5% $H_2O$, 2.5% TIS, and 2.5% ethanedithiol (EDT) (Sigma) for 3 h at room temperature to achieve global deprotection and cleavage from the resin. The crude peptide products were precipitated and washed with cold anhydrous $Et_2O$ (Fisher). The precipitates were resuspended in water and lyophilized. The products obtained were then resuspended in 0.1% aqueous TFA/acetonitrile. The peptides were analyzed and purified by reverse-phase HPLC. HPLC analysis was performed on a Hewlett-Packard 1200 series instrument and an analytical Vydac C18 column (5 µm, 4×150 mm). The flow rate was 1 mL/min, and detection was at 214 nm and 550 nm. Semi-preparative HPLC was performed on a Vydac C18 10×250 mm column. The flow rate was 4 mL/min, and detection was at 214 nm and 550 nm. All runs used linear gradients of 0.1% aqueous TFA (solvent A) and 90% acetonitrile, 9.9% water, and 0.1% TFA (solvent B). The correct identity of the peptides was confirmed by MALDI-TOF performed with a Shimadzu/Kratos instrument (AXIMA-CFR, Shimadzu, Kyoto). TAT, expected mass: 2039.16, observed mass: 2040.66. DEAC-K9, expected mass: 1412.97, observed mass: 1415.59.

Synthesis of Acetamidated C(S—$CH_2CONH_2$)K(ε-NH-TMR)TAT

C(S—$CH_2CONH_2$)K(ε-NH-TMR)TAT was formed after addition of iodoacetamide (Sigma) (0.275 mg, 1.49 µmol) to CK(ε-NH-TMR)TAT (148 µg, 0.074 µmol) in 25 mM HEPES pH 7.5. The reaction was performed under an atmosphere of $N_2$ and was monitored by analytical reverse-phase HPLC and MALDI-TOF. The product was purified using analytical reverse-phase HPLC. Expected mass: 2096.18, observed mass: 2096.31.

Generation of dTAT by Dimerization of CK(TMR)TAT (TAT)

dTAT was formed by dissolving (0.3 mg, $1.5 \times 10^{-4}$ mmol) TAT in aerated phosphate buffer saline (PBS) pH 7.4 (5 mL). Oxygen dissolved in the buffer act to oxidize the thiol groups on the peptides and form a disulfide bond. The reaction was allowed to react overnight and was monitored by analytical reversed-phase HPLC and MALDI-TOF. The product was purified using analytical reverse-phase HPLC. Expected mass: 4076.30, observed mass: 4084.21.

Cloning, Overexpression and Purification of TAT-Cre, TAT-mCherry, HoxB4, and TAT-HoxB4

The pTriEx-HTNC plasmid encoding His-tagged TAT-NLS-Cre (TAT-Cre) protein was purchased from Addgene (Cambridge, Mass.). The TAT-Cre gene was then cloned into pTXB1 vector and transformed into *E. coli* BL21 (DE3) cells (Agilent Technologies, Santa Clara, Calif.). The protein was expressed and purified as described in Peitz, M., et al., "Ability of the hydrophobic FGF and basic TAT peptides to promote cellular uptake of recombinant Cre recombinase: A tool for efficient genetic engineering of mammalian genomes," *Proceedings of the National Academy of Sciences of the United States of America* 99:4489-4494 (2002), incorporated herein by reference in its entirety. Briefly, TAT-Cre was expressed with 1 mM IPTG at 37° C. for 3 h. TAT-Cre was then purified to homogeneity using a Ni-NTA resin (Qiagen, Valencia, Calif.) and cation exchange chromatography (HiTrap SP HP, GE Healthcare, Pittsburgh, Pa.). pTXB1-TAT-mCherry was obtained by inserting the TAT DNA sequence into the pTXB1-mCherry plasmid. The oligonucleotides with sequences 5'-TAT GGG TCG TAA AAA ACG TCG TCA GCG TCG TCG TGG TCA-3' (SEQ ID NO:2) and 3'-ACC CAG CAT TTT TTG CAG CAG TCG CAG CAG CAC CAG TAT-5' (SEQ ID NO:3) (IDT, Coralville, Iowa) coding for the TAT sequence, which contain NdeI sites, were annealed to generate dsDNA. The pTXB1-mCherry plasmid was cut with NdeI (New England Bio-Labs, Ipswich, Mass.) and ligated with TAT dsDNA. The pTXB1-TAT-mCherry plasmid was transformed into BL21 (DE3) cells and protein expression was induced with 1 mM IPTG at 16° C. for 24 h. Cells were harvested and resuspended in lysis buffer containing 20 mM Tris-Cl (pH 7.5) and 200 mM NaCl. After cell lysis by sonication and high-speed centrifugation at 15K RPM for 1 h, the soluble fraction was applied to chitin resin (New England BioLabs, Ipswich, Mass.) pre-equilibrated with lysis buffer and incubated overnight at 4° C. (the protein contains a C-terminal intein-chitin binding domain purification tag). The resin was washed with 10 column volumes of lysis buffer. The protein was cleaved from the resin by incubating the beads with 1 column volume of cleavage buffer supplemented with 100 mM 2-mercaptoethanesulfonic acid and for 24 hr at 4° C. The protein was further purified using cation exchange chromatography. The pTAT-HA-HoxB4 vector was generously provided by G. Sauvageau, Montreal University, Montreal, Quebec, Canada. His$_{(6)}$-HoxB4 was produced by cloning the HoxB4 gene into pET-28a. Briefly, the HoxB4 cDNA was first amplified from pTAT-HA-HOXB4 by using primers designed to introduce the NdeI & XhoI sites, at the 5' and 3' ends, respectively (5'-GGC ATT CAT ATG GCT ATG AGT TCT TTT TTG ATC AAC TCA-3' (SEQ ID NO:4); 5'-GGT CAG TCT CGA GCT AGA GCG CGC GGG G-3') (SEQ ID NO:5) (IDT). The PCR fragment was then inserted into the corresponding NdeI & XhoI sites of the 6×His-tag vector, pET-28a. The fidelity of the reading frame was confirmed by sequencing. The procedure for the purification of both TAT-HoxB4 and HoxB4 is similar and has been previously described in Krosl, J, et al., "In vitro expansion of hematopoietic stem cells by recombinant TAT-HOXB4 protein," *Nat Med* 9:1428-1432 (2003), incorporated herein by reference in its entirety. Briefly, BL21 (DE3) cells were transformed with either pTAT-HAHoxB4 or pET28a-HoxB4 and induced at 37 C for 5 hours with 1 mM IPTG. The pelleted cells were lysed by sonication in Buffer A (8 M Urea, 20 mM HEPES, 200 mM NaCl, pH 8.0). Lysates, which were obtained via high-speed centrifugation (14K RPM, 30 minutes at 22° C.), were then adjusted to 10 mM imidazole and incubated with Ni-NTA Agarose beads for 60 minutes at room temperature. The nickel beads were then washed with Buffer A containing 20 mM and 40 mM imidazole to eliminate the presence of any non-specific products and bound proteins were subsequently eluted with 100 mM and 250 mM imidazole in Buffer A. Eluates from both concentrations of imidazole containing the proteins of interest (i.e., TAT-HoxB4 or HoxB4) were loaded on a HiTrap SP HP column at 4° C. in Buffer B (4 M Urea, 20 mM HEPES, 50 mM NaCl, pH 6.5) and eluted on the FPLC in a single-step at 4° C. with Buffer C (20 mM HEPES, 1 M NaCl, pH 8.0). Both proteins were immediately desalted by diluting with 20 mM HEPES (pH 8.0) and concentrated using centrifugal filter units with 10K MWCO (EMD Millipore, Billerica, Mass.), aliquoted and flash-frozen at −80° C. Protein concentrations were determined using the Bradford protein assay (Bio-Rad, Hercules, Calif.).

Delivery of Peptides Inside Live Cells

Live cells from different lines (HeLa, HaCat, NIH 3T3) were grown in Dulbecco's Minimum Essential Media (DMEM) (Fisher) supplemented with 10% fetal bovine serum (FBS) (Fisher) and kept at 37° C. in a humidified atmosphere containing 5% $CO_2$. Cells were then seeded in 8-well dishes so that the cells were 80%-90% confluent after 48 h. Each well was washed 3 times with PBS and Leibovitz's L-15 medium that did not contain the amino acid cysteine (non-reducing L-15, nrL-15). The media (nrL-15) used for incubation lacks cysteine to avoid reduction of the disulfide bond of dTAT. Cells were then incubated with different concentrations of the acTAT, TAT, or dTAT at 37° C. for 1 h. Cells were washed 3 times with PBS and nrL-15 and placed on an inverted epifluorescence microscope (Model IX81, Olympus, Center Valley, Pa.) equipped with a heating stage maintained at 37° C. Images were collected using a Rolera-MGI Plus back-illuminated EMCCD camera (Qimaging, Surrey, BC, Canada). Images were acquired using bright field imaging and three standard fluorescence filter sets: CFP (Ex=436±10 nm/Em=480±20 nm), RFP (Ex=560±20 nm/Em=630±35 nm), and FITC (Ex=488±10 nm/Em=520±20 nm). The fluorescence intensities of different cells were measured with the SlideBook 4.2 software (Olympus, Center Valley, Pa.) and the average fluorescence intensity was determined for each condition. It has been previously reported that CPPs labeled with fluorophores such as TMR can photosensitize membranes and cause endosomal leakage upon light irradiation. See, Srinivasan, D. et al., "Conjugation to the cell-penetrating peptide TAT potentiates the photodynamic effect of carboxytetramethylrhodamine," *PloS one* 6:e17732 (2011) and Muthukrishnan, N., et al., "Synergy Between Cell-Penetrating Peptides and Singlet Oxygen Generators Leads to Efficient Photolysis of Membranes," *Photochemistry and Photobiology* 89:625-630 (2012), each incorporated herein by reference in its entirety. Light exposure of dTAT trapped inside endosomes (e.g., after incubation at 2 µM) can also cause endosomal leakage (not shown). However, several pieces of evidence indicate that light does not play a significant role in the activity of dTAT reported herein. First, all delivery experiments were performed under conditions of minimal light irradiation (dark room with dim red light). When fluorescence imaging is required, probes (e.g., SNAP surface 488, EGFP) are imaged before dTAT is, thereby minimizing the possible effect of light on endosomal release. For experiments performed with Cre and Hoxb4, cells are not imaged and not exposed to light (not at all for Hoxb4, 12 h after incubation for Cre). In addition, the light dose required to observe light-induced endosomal leakage is typically 10 to 20 fold greater than that used for imaging.

Delivery of Small Molecules, Peptides and Proteins Inside Live Cells by Coincubation with dTAT HeLa cells were seeded in 8-well dishes, grown and washed as described in the prior section. Cells were then co-incubated with 5 M delivery peptide and with the cargo at the corresponding concentration for 1 h at 37° C. Cells were washed 3 times with PBS and nrL-15 and placed on the microscope. Images were acquired as described before. For transfection and expression of SNAP-H2B and TagCFP-mito, plasmids were mixed with Lipofectamine™ 2000 reagent in opti-MEM media and incubated at room temperature for 30 min. The DNA complex was added to previously seeded HeLa cells (80% confluent) on an 8-well dish and cells were kept at 37° C. for 24 h. After 24 h, the wells were washed 3 times with PBS and nrL-15 prior to performing the delivery experiments using the SNAP-Surface® 488 or FITC-anti-ATP5A.

Quantitative Determination of Peptide and Uptake Inside Cells

HeLa cells were seeded in a 48 well dish, grown and washed as described above. For the peptide uptake experiment, each well was incubated for 1 h with varying concentration of acTAT, TAT or dTAT (range: 5-25 µM peptide concentration). For the titration experiment, cells were incubated with dTAT (5 µM) and varying concentrations of DEAC-K9 (range: 1-20 µM). Cells were then washed with PBS and nrL-15 and imaged. Multiple images for each condition were obtained and processed. To lyse cells, nrL-15 was removed from the wells and a total of 100 μL of HeLa cell lysis Buffer (50 mM Tris pH 7.5, 2 mM EDTA, 2 mM DTT, 0.1% Triton X-100) was incubated with cells for 5 min. The cells were lysed and scraped off the dish and pipetted into a 1.5 mL microcentrifuge tube. The cell lysates were centrifuged at 13.2K RPM for 25 min. For the uptake experiment, 70 μl of the supernatants from each condition were collected and placed in a 96 well plate. The fluorescence from the cell lysates were measured using a plate reader equipped with a fluorescence module (Ex=525, Em=580-640 nm) (GloMax®-Multi+ Detection System, Promega, Fitchburg, Wis.). For the titration experiment, 80 μL of supernatant was diluted to a total volume of 100 μL and the bulk fluorescence was measured using a SLM-8000C fluorometer (Ex=435 nm, Em=465-475 nm) (SLM Instruments, Bath, UK). The fluorescence emission was averaged and recorded. The data was normalized to total protein concentration in each well using the Bradford Protein Assay. Using a 96 well plate, 10 μL of each cell lysate was added to 200 μL of a 1× protein assay reagent and incubated at room temperature for 30 min. The absorbance at 600 nm was measured using the plate reader. Measurements were repeated in triplicate.

Quantitative Analysis of TAT-HoxB4 & HoxB4 Delivery with TAT and dTAT Using a Luciferase Reporter The murine fibroblast cell line (NIH-3T3, stably transfected with the E2A-PBX vector), the luciferase reporter vector, pML (5×HOX/PBX; contains a promoter with binding sites for HOXB4 and PBX) and the β-gal internal control vector used in the following studies were kindly provided by P. Zandstra (University of Toronto, Ontario, Canada). The cells were initially cultured in 100 mm dishes at 37° C. with 5% $CO_2$ in DMEM supplemented with 10% FBS. For experimental purposes, however, cells were seeded in 24-well plates at a density of 5-6×$10^4$ cells/well for 24 hours. Subsequently, cells were co-transfected with 0.8 μg/mL of pML (5×HOX/PBX) and of the β-gal internal control vector using Lipofectamine 2000. Twelve hours post-transfection, cells were washed and incubated with TAT-HoxB4 or HoxB4 (both at 200 nM, unless otherwise noted; see below) with or without TAT or dTAT in nrL-15 for 90 min. Some cells were also incubated with TAT-mCherry (200 nM) with and without the peptides. After incubation, all cells were washed with PBS and lysed according to the manufacturer's protocol for the reporter lysis buffer (RLB) (Promega). For titration experiments, the same protocol was followed, with the exception that HoxB4 concentrations were varied (25, 50, 100, 150 and 200 nM). In order to quantitate the luciferase reporter activity, 100 μL of luciferase assay reagent (Promega) was added to 20 μL of cell lysate and bioluminescence was immediately measured using a SpectraMaxL luminometer (Sunnyvale, Calif.). For the purposes of measuring transfection efficiency, 180 μL of β-gal assay buffer was mixed with 20 μL of cell lysate in a 96-well plate and incubated at 37° C. for 30 min. The β-gal assay buffer is comprised of 75% 0.1 M sodium phosphate, pH 7.5, 24% o-nitrophenyl β-D-galactopyranoside (ONPG made at a concentration of 4 mg/mL in 0.1 M sodium phosphate) (Sigma) and 1% 100-fold solution (10% 1 M magnesium chloride solution, 32% β-mercaptoethanol, and 58% distilled water). Absorbance was then measured at 450 nm using the plate reader. Since the absorption spectrum of the chromophore (TMR) conjugated to the peptide used in this study overlaps with that of β-gal, 20 μL of cell lysate containing the peptide was also diluted with 180 μL of the lysis buffer and absorbance values obtained at 450 nm were subtracted from that of the β-gal absorbance values. The luciferase activity of all samples was determined as a ratio of the luciferase activity to the β-gal activity and the fold-increase in luciferase activity was established by normalizing the luciferase activity of each sample to that of cells, which were transfected, but had no protein delivered.

Cell Viability Assays

In order to determine cells that had compromised plasma membranes, cells were treated with SYTOX® Green (SYTOX® Blue in some cases) and Hoechst (Invitrogen, Carlsbad, Calif.). SYTOX® dyes are cell-impermeable and stain the DNA of cells with compromised plasma membranes. The Hoechst dye is cell permeable and stains the DNA of all cells. Images were acquired using the green and blue filter. The green and blue images were used to count cells with a blue or green stained nucleus. Image J was used to count the dead (green) and total cells (blue). Cytotoxicity was determined from the ratio of SYTOX® Green positive cells/total number of cells. An MTT-assay was performed to determine the effect of the peptide on cell proliferation. Cells were seeded in a 6-well dish, grown and washed as described above. One well from the dish was incubated with 5 μM dTAT at 37° C. for 1 h. A second well was left untreated and served as control. Cells were washed 3 times with PBS and nrL-15. Cells were trypsinized and seeded into 96-well dishes containing 200 μL of DMEM. The cells were then allowed to attach to the bottom of the dish for 12 h. The MTT assay was then performed at specific time points to measure cell proliferation. The DMEM was removed, replaced with 100 μL of nrL-15, and 10 μL, of a 12 mM MIT stock solution was added to the wells. The 96-well dish was incubated at 37° C. for 4 h. After the incubation, 100 μL of a 10 mM SDS-HCl solution was added to each well. The solution was mixed thoroughly by pipetting up and down and incubated for 13 h. After the incubation each sample was mixed and the absorbance at 600 nm was measured. Controls included a negative control where 10 μL MTT was added to 100 μL of nrL-15 alone (no cells). A second control consisted of cells treated with the delivery peptide but to which no MTT was added to subtract the contribution of TMR from the measured absorbance. The absorbance of the negative control was subtracted from all samples.

Determination of dTAT and Cargo Interactions

Fluorescence emission spectra were obtained using an SLM-8000C fluorometer upgraded with the phoenix package (ISS, Champaign, Ill.) and Vinci v.1.6 PC software (ISS). The experiments were conducted using a quartz cuvette at room temperature. The samples were excited at 488 nm (slit width=1 mm) and the fluorescence emission was scanned from 500 to 650 nm (slit width=1 mm). All samples (EGFP (1 μM) and dTAT (5 μM)) were prepared using nrL-15.

While the illustrative embodiments have been illustrated and described, it will be appreciated that various changes can be made without departing from the spirit and scope of the disclosure.

The embodiments of the invention in which an exclusive property or privilege is claimed are defined as follows:

1. A compound having the formula:

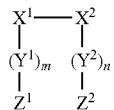

wherein
X is a linking moiety,
Y is an amino acid residue covalently coupled to a hydrophobic moiety,
Z is a cell-penetrating peptide (CPP) moiety, wherein the CPP moiety has a net positive charge and has an amino acid sequence with 50% or more residues having a guanidinium group, and
m and n are independently 0 or 1.

2. The compound of claim 1, wherein the CPP moiety comprises between 3 and 30 amino acids.

3. The compound of claim 2, wherein the CPP moiety comprises an amino acid sequence with at least 85% identity to the sequence set forth in SEQ ID NO:1.

4. The compound of claim 3, wherein the CPP moiety comprises the amino acid sequence set forth in SEQ ID NO:1.

5. The compound of claim 1, wherein at least one of m and n is 1.

6. The compound of claim 5, wherein the hydrophobic moiety comprises a $C_6$-$C_{30}$ straight chain, branched, or cyclic group.

7. The compound of claim 6, wherein the group includes one or more heteroatoms selected from N, O, and S.

8. The compound of claim 6, wherein the cyclic group is mono-, bi-, or tricyclic.

9. The compound of claim 6, wherein the hydrophobic moiety comprises a rhodamine group.

10. The compound of claim 9, wherein the rhodamine group is tetramethylrhodamine (TMR).

11. The compound of claim 5, wherein the amino acid residue is lysine (K).

12. The compound of claim 1, wherein m and n are 0, and wherein $Z^1$ and/or $Z^2$ is a CPP that comprises an amino acid residue linked to a hydrophobic moiety.

13. The compound of claim 12, wherein the amino acid residue is the N-terminal most lysine (K) residue in the CPP amino acid sequence.

14. The compound of claim 1, wherein X is a cysteine (C) residue.

15. The compound of claim 14, wherein $X^1$ and $X^2$ are cysteine (C) residues linked by a disulfide bond.

16. The compound of claim 1, wherein X, Y, and/or Z are linked by amide bonds.

17. The compound of claim 1, wherein the CPP of $Z^1$ and the CPP of $Z^2$ have amino acid sequences having at least 85% identity to each other.

18. The compound of claim 1, wherein the combination of X—Y—Z comprises no more than 30 amino acid residues.

19. The compound of claim 1, wherein the compound is capable of facilitating endosomal lysis.

20. A method of delivering a cell-impermeable molecule to the cytosol of a cell, the method comprising contacting a cell with a compound of claim 1 and a cell-impermeable molecule under conditions sufficient to permit endocytosis.

21. The method of claim 20, wherein the cell is contacted with a concentration of the compound of at least 1 μM.

22. The method of claim 20, wherein the cell-impermeable molecule is a peptide, a polymer including polypeptides and nucleic acids, or a small-molecule pharmaceutical.

23. The method of claim 22, wherein the polypeptide is a transcription factor.

24. The method of claim 20, wherein the cell-impermeable molecule is not covalently linked to the compound.

25. The method of claim 20, wherein the cell-impermeable molecule has a net positive charge.

26. The method of claim 20, wherein the cell is obtained from a living subject and is contacted with the compound and cell-impermeable molecule ex vivo.

27. The method of claim 20, wherein the cell is in a living subject and is contacted with the compound and cell-impermeable molecule in vivo.

28. The method of claim 27, wherein the cell is contacted in vivo by administering an amount of the compound to the subject effective to deliver a cell-impermeable molecule to the cytosol of the cell.

29. The method of claim 20, wherein the cell is in or is obtained from a mammalian subject.

30. A method of inducing pluripotency in a cell ex vivo, the method comprising contacting a cell obtained from a subject with the compound of claim 1 and a transcription factor under conditions sufficient to allow endocytosis, and culturing the cell to obtain pluripotency of the cell.

31. A method of expanding a stem cell ex vivo, the method comprising contacting a stem cell with the compound of claim 1 and a transcription factor under conditions sufficient to allow endocytosis, and culturing the cell to obtain expansion of the cell.

\* \* \* \* \*